(12) United States Patent
Carmi et al.

(10) Patent No.: US 10,098,736 B2
(45) Date of Patent: Oct. 16, 2018

(54) IMPLANT INTENDED FOR POSITIONING IN A BLOOD FLOW PASSAGE AND ASSOCIATED TREATMENT DEVICE

(71) Applicant: LABORATORIES INVALV, Dury (FR)

(72) Inventors: Doron Carmi, Amiens (FR); Marcel Peltier, Dury (FR)

(73) Assignee: LABORATOIRES INVALV, Dury (FR)

( * ) Notice: Subject to any disclaimer, the term of this patent is extended or adjusted under 35 U.S.C. 154(b) by 827 days.

(21) Appl. No.: 14/278,665

(22) Filed: May 15, 2014

(65) Prior Publication Data

US 2014/0249622 A1    Sep. 4, 2014

Related U.S. Application Data

(63) Continuation-in-part of application No. PCT/EP2012/072910, filed on Nov. 16, 2012.

(30) Foreign Application Priority Data

Nov. 17, 2011 (FR) .................................. 11 60482

(51) Int. Cl.
*A61F 2/24* (2006.01)
*A61B 17/04* (2006.01)

(52) U.S. Cl.
CPC .......... *A61F 2/2442* (2013.01); *A61F 2/2418* (2013.01); *A61F 2/2436* (2013.01);
(Continued)

(58) Field of Classification Search
CPC ............ A61F 2/2418; A61F 2250/0039; A61F 2/2409; A61F 2/2427; A61F 2/2457;
(Continued)

(56) References Cited

U.S. PATENT DOCUMENTS 8,414,644 B2    4/2013   Quadri et al.
8,685,086 B2    4/2014   Navia et al.
(Continued)

OTHER PUBLICATIONS

International Search Report for PCT/EP2012/072910 dated Feb. 4, 2013.

*Primary Examiner* — Ann Schillinger
(74) *Attorney, Agent, or Firm* — B. Aaron Schulman, Esq.; Stites & Harbison, PLLC

(57) ABSTRACT

The implant (12) according to the invention comprises a tubular frame (16), a plurality of distal arms (18) capable of pressing on a first face of a tissue, and a plurality of proximal arms (20) having an end (62) connected to the frame and a free end (64) intended to press on a second face of the tissue to clamp the tissue. The implant comprises a first integral assembly including a first part (38) of the frame and the proximal arms (20), and a second integral assembly including a second part of the frame (40) and the distal arms (18), the first assembly and the second assembly being attached one on top of the other. The first part (38) of the frame is in the form of a proximal sleeve, extending longitudinally between a proximal end (41) and a distal end (43) of the sleeve. The connected end (62) of each proximal arm (20) is connected to the distal end (43) of the proximal sleeve (38), and the free end (64) of each proximal arm (20) extends beyond that distal end (43) of the proximal sleeve (38).

13 Claims, 19 Drawing Sheets

(52) U.S. Cl.
CPC . *A61F 2220/0008* (2013.01); *A61F 2230/005* (2013.01); *A61F 2230/0054* (2013.01); *A61F 2250/0063* (2013.01)

(58) Field of Classification Search
CPC .... A61F 2002/826; A61F 2/24; A61F 2/2412; A61F 2/2445; A61F 2/844; A61F 2/915
See application file for complete search history.

(56) References Cited

U.S. PATENT DOCUMENTS

| | | |
|---|---|---|
| 2011/0153008 A1 | 6/2011 | Marchand et al. |
| 2011/0224785 A1* | 9/2011 | Hacohen ............ A61B 17/0401 623/2.18 |
| 2011/0313515 A1 | 12/2011 | Quadri et al. |
| 2012/0078360 A1* | 3/2012 | Rafiee ................... A61F 2/2418 623/2.37 |
| 2012/0303116 A1 | 11/2012 | Gorman, III et al. |

\* cited by examiner

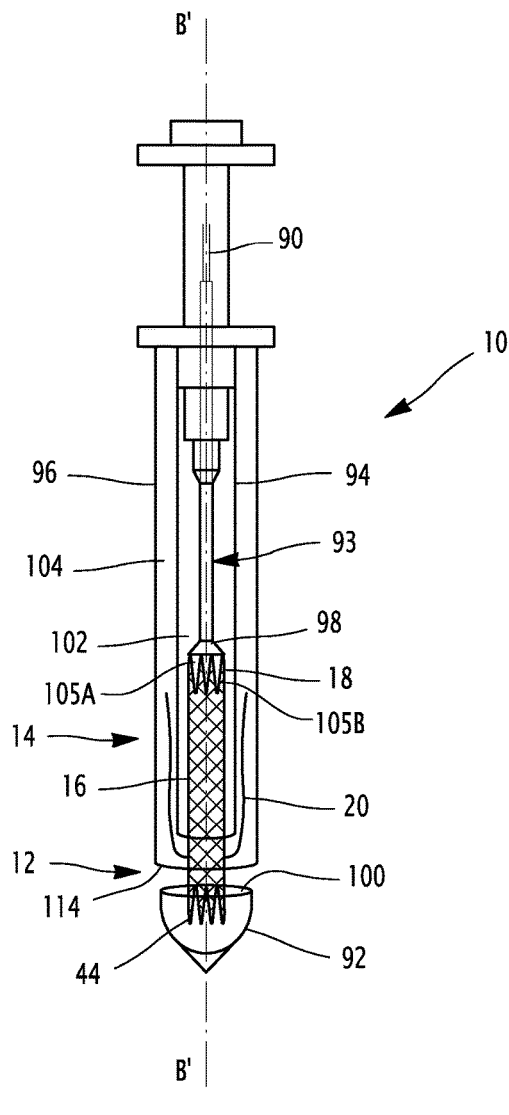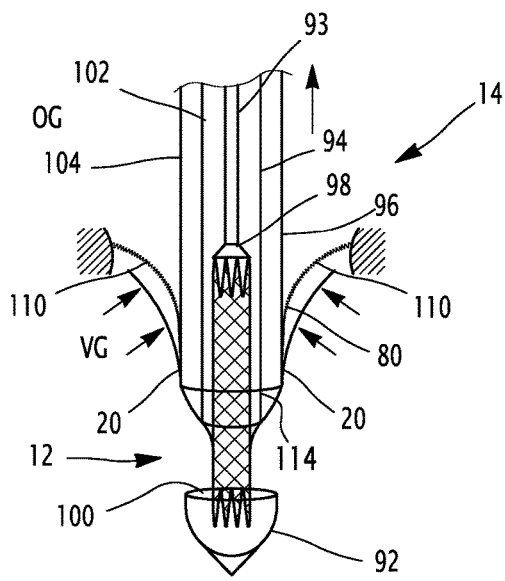
FIG.7
FIG.8

IMPLANT INTENDED FOR POSITIONING IN A BLOOD FLOW PASSAGE AND ASSOCIATED TREATMENT DEVICE

CROSS REFERENCE TO RELATED APPLICATIONS

This application is a Continuation-in-Part of International Application No. PCT/EP2012/072910, filed Nov. 16, 2012 (which is hereby incorporated by reference).

The present invention relates to an implant designed to be placed in a blood flow passage, the implant being deployable between a contracted configuration and a deployed configuration, comprising:
- a tubular frame with a central axis defining an inner blood flow conduit, the tubular frame extending between a proximal end and a distal end;
- a plurality of distal arms extending perpendicular to the central axis in the deployed configuration to press on a first face of the tissue;
- a plurality of proximal arms having an end connected to the frame and a free end designed to press on a second face of the tissue to clamp the tissue.

Such an implant is designed to replace a native heart valve, in particular a mitral valve or a tricuspid valve, with an endovalve.

In the case of the mitral valve, the implant is designed to be placed in an atrio-ventricular blood passage of a human or animal heart.

During systole, the blood passage between the left atrium and left ventricle of the heart is interrupted by the closing of a native heart valve present in a mitral system. This valve ensures one-way circulation of the blood flow, avoiding reflux at the end of the ventricular contraction.

The mitral system comprises a mitral annulus, two valve leaflets connected to that annulus, and a sub-valve system comprising chords and piers.

The valve leaflets include an anterior leaflet, or "large mitral valve", and a posterior leaflet, or "small mitral valve".

The part connecting the annulus with the large valve is fibrous, while the part connecting the annulus with the small valve is muscular. The large and small valves are connected to the ventricular part by chords, which in turn are connected to piers. In diastole, the two leaflets open to free the passage between the atrium and the left ventricle.

In systole, the ventricular contraction causes a sharp increase in the left intra-ventricular pressure, causing blood to be ejected through the aortic valve. At the same time, the contraction of the piers and tensing of the chords cause the two leaflets to be joined, so as to sealably isolate the left atrial and ventricular cavities.

However, diseases affect the valves and the chords. In particular, the latter may suffer degeneration, thereby allowing reflux or regurgitation.

Furthermore, in case of severe and chronic mitral regurgitation, the underlying left ventricle expands and its contractility decreases, which may lead to the need for heart surgery, even without any symptoms.

To offset these problems, it is known to implant an endovalve between the leaflets delimiting the sick valve. The endovalve is for example made up of a deployable tubular endoprosthesis and a flexible closing member made from a tissue of animal origin. The flexible closing member is permanently fixed in the endoprosthesis.

Such endovalves are generally implantable less invasively than a surgical valve replacement, which limits the risks associated with the implantation of the valve, in particular in terms of mortality.

Known for example from WO 2010/121076 is a mitral implant positioned in an atrio-ventricular blood passage to replace the native valve.

Such an implant includes a plurality of atrial arms and a plurality of ventricular arms positioned across from the atrial arms to clamp the mitral annulus, while pressing on the atrial face of the leaflets of the native valve, plicating it. The ventricular arms are formed by hooks positioned at the ventricular end of the frame and folded toward the atrial end. The atrial arms are formed by V-shaped loops extending across from the ventricular arms, in the vicinity thereof, but moving away from the frame and the atrial arms.

The free ends of the ventricular arms and the atrial arms are positioned separated from each other and are respectively pushed into an atrial face and into a ventricular face of the mitral annulus.

Another example implant is in particular described in WO 2011/057087.

It will be noted that the installation of a mitral implant to replace the native valve may be done by passing through the atrial cavity, or alternatively by passing through the ventricular cavity. This installation is generally done using a suitable deployment tool. The structure of this deployment tool may be different based on the side (atrial or ventricular) through which one passes to perform this installation.

The invention in particular aims to facilitate the installation of a mitral implant, in particular when the latter is installed by passing through the ventricular cavity.

To that end, the invention in particular relates to an implant designed to be placed in a blood flow passage, and to be fixed on a tissue, the implant being deployable between a contracted configuration and a deployed configuration, the implant comprising:
- a tubular frame along a central axis, defining an inner blood flow conduit, the tubular frame extending between a proximal end and a distal end;
- a plurality of distal arms extending perpendicular to the central axis in the deployed configuration to press on a first face of the tissue;
- a plurality of proximal arms having one end connected to the frame and one free end designed to press on a second face of the tissue to clamp the tissue;

characterized in that
- the implant comprises a first integral assembly including a first part of the frame and the proximal arms, and a second integral assembly including a second part of the frame and the distal arms, the first assembly and the second assembly being attached one on top of the other;
- the first part of the frame is in the form of a proximal sleeve, with a central axis, extending longitudinally between a proximal end and a distal end of the sleeve;
- the connected end of each proximal arm is connected to the distal end of the proximal sleeve, and the free end of each proximal arm extends in the direction of the central axis beyond that distal end of the proximal sleeve.

Each proximal arm extends from the distal end of the proximal sleeve, beyond that distal end. Thus, when the proximal sleeve is brought closer to the valve leaflets from the ventricular cavity, the proximal arms are located in front of that sleeve, with the result that they can receive the valve leaflets without being bothered by the sleeve.

In other words, the implant structure as defined above allows greater ease of insertion of the valve leaflets into the receiving space delimited by the proximal arms.

It should be noticed that since the frame is made of the first part and the second part, this frame can be considered as built only when said first and second parts are assembled together.

The implant according to the invention may comprise one or more of the following features, considered alone or according to any technically possible combination:

- The proximal arms delimit a space between them for receiving the tissue, the proximal sleeve extending completely outside that receiving space.
- The first and second parts of the frame are each formed by a mesh of interlaced threads, for example delimiting polygonal meshes.
- The proximal arms delimit a space between them for receiving the tissue, the second part of the frame being in the form of a distal sleeve, with a central axis, said distal sleeve extending longitudinally: partially inside the proximal sleeve, coaxially to the proximal sleeve; partially inside the space for receiving the tissue, such that the tissue is capable of being received between the proximal arms and the distal sleeve; and partially beyond the tissue receiving space.

Optionally, in the deployed configuration, when no outside bias is present, the free end of at least one proximal arm is positioned in contact with the distal arm and/or the frame, the proximal arm including at least one intermediate region extending along and radially separated from the frame to define a longitudinal cavity for receiving the tissue.

In fact, it appears that an implant of the state of the art, for example as described in WO 2010/121076, is not fully satisfactory. In particular, the connecting parts connecting the annulus with the large valve being fibrous, the annular and ventricular arms are planted in a tissue that is not very robust.

The axial fixing of the implant is therefore weakened, and its positioning may evolve over time, in particular under the effect of the blood pressure applied on the valve, causing a secondary movement of the implant.

Furthermore, the fastening of the implant on the entire mitral annulus creates a risk, across from its interior area, of bother for the blood flow across from the left ventricular ejection pathway delimited by that interior area.

In the case mentioned above where the implant according to the invention has at least one proximal arm whereof the free end is positioned in contact with a distal arm and/or the frame, and where the proximal arm includes at least one intermediate region, an implant is obtained designed to be implanted to replace a defective native valve, in particular a mitral valve, that has a simple structure, while offering robust fixing on a tissue of the native valve.

In particular, in the case of a mitral valve, wider fixing is thus offered on the surface of the two leaflets and its two atrial or distal, and ventricular proximal, faces, with an off-centered position of the mitral implant moving away from the interior area of the mitral annulus and advantageously pressing on its posterior area.

Advantageously, the implant according to the invention has at least one proximal arm whereof the free end is positioned both in contact with a distal arm and in contact with the frame. Thus, the proximal arm has several bearing points, with the result that the implant is more stably anchored.

The implant according to the invention may further comprise one or more of the following features, considered alone or according to any technically possible combination:

- The intermediate region of each proximal arm has a curved shape, with the convex side oriented radially away from the axis, the immediate region comprising at least one proximal segment diverging radially away from the connected end and at least one distal segment converging radially toward the free end.
- At least one proximal arm defines, at its free end, a distal region protruding radially away from the central axis relative to the intermediate region, the distal region being pressed below a distal arm, the stiffness in flexure of the intermediate region preferably being greater than the stiffness in flexure of the distal region.
- Each proximal arm has two branches distally converging toward one another to substantially assume the shape of an upside down V in the deployed configuration.
- Each distal arm forms a loop protruding transversely relative to the central axis.
- The distal arms are adjacent to one another to form a transverse collar perpendicular to the axis in the deployed configuration, the collar advantageously being covered with a skirt made from tissue capable of guiding the blood through the frame.
- The radial expanse of a first distal arm in a first annular sector around the axis is greater than the radial expanse of a second distal arm situated in a second annular sector, advantageously greater than 50% of the radial expanse of a second distal arm.
- At least one first proximal arm has a first distal region pressed across from a first distal arm, a second proximal arm having a second distal region pressed across from a second distal arm, the radial expanse of the first distal region being greater than the radial expanse of the second distal region.
- The proximal sleeve has, when it is separated from the distal sleeve, and when no outside bias is present, a diameter smaller than that of the distal sleeve when no outside bias is present.
- Each proximal arm is radially movable away from the central axis from an idle position in contact with a distal arm and/or the frame toward a radially separated position for the insertion of the tissue into the cavity, the proximal arm being elastically biased toward the idle position, or alternatively being biased toward the idle position by any possible mechanical means.
- The length of the or each proximal arm, considered between its end connected to the frame and its free end along the axis A-A', is greater than 50%, advantageously greater than 70%, of the length of the frame, taken between the proximal end and the distal end.
- The implant includes a flexible closing member mounted in the inner conduit to selectively close the blood passageway.
- The implant is a single piece made integrally.
- The intermediate region defining the longitudinal cavity is situated between the connected end and the point of contact of the free end with the frame and/or the distal arm.
- The distal region is situated axially opposite the intermediate region relative to the point of contact of the free end with the frame and/or the distal arm.

The invention also relates to a treatment device for a blood flow passage, characterized in that it includes:

an implant as defined above;

a tool for deploying the implant, the implant being mounted in its contracted configuration in the deployment tool.

The treatment device according to the invention may include one or more of the following features, considered alone or according to any technically possible combination:

The device includes a locking head delimiting at least one housing for receiving the frame, a stent engaged in the frame, an inner sheath for retaining each distal arm in an axial configuration positioned around the frame, and an outer sheath for pressing each proximal arm against the outer sheath, the inner sheath being positioned around the frame and each distal arm to keep the distal arm in an axial configuration.

The device includes a locking head delimiting at least one housing for receiving the frame and retaining each distal arm in an axial configuration, a stent engaged through the frame, an outer sheath for pressing the proximal arm against the frame, the frame and the distal arms being substantially immobile relative to the stent during the movement of the outer sheath, the device further including an intermediate wall protruding from the head in the outer sheath to keep the proximal arms in position and separate them from the distal arms.

The device includes: a locking head delimiting at least one housing for receiving the frame, a stent engaged in the frame, comprising a distal end fixed to the locking head, an inner sheath for retaining the second part of the frame in the contracted configuration, the inner sheath being positioned around the second part of the frame, an outer sheath for pressing each proximal arm against the outer sheath, the outer sheath being positioned around the proximal arms, and an intermediate sheath for keeping the first part of the frame in the contracted configuration, the intermediate sheath being positioned around the first part of the frame, said first part being positioned between the inner sheath and the intermediate sheath.

The invention also relates to a method for placing an implant in a blood flow passage and to fix it on leaflets of a native valve, between an atrial cavity and a ventricular cavity of a hearth, said leaflets having an atrial face and a ventricular face, and said implant being deployable between a contracted configuration and a deployed configuration, the implant comprising:
- a tubular frame along a central axis, defining an inner blood flow conduit, the tubular frame extending between a proximal end and a distal end, the tubular frame comprising a first part and a second part, said first and second parts being separated and said first and second parts being assemblable so as to form the tubular frame when assembled;
- a plurality of distal arms extending perpendicular to the central axis in the deployed configuration to press on the atrial face of the leaflets;
- a plurality of proximal arms having one end connected to the frame and one free end (64) designed to press on the ventricular face of the leafleats to clamp the leaflets;
- a first integral assembly including the first part of the frame and the proximal arms, and a second integral assembly including the second part of the frame and the distal arms;

wherein:
- the first part of the frame is in the form of a proximal sleeve, with a central axis, extending longitudinally between a proximal end and a distal end of the sleeve;
- the second part of the frame is in the form of a distal sleeve, the proximal sleeve being slidably movable relative to the distal sleeve while not assembled,
- the connected end of each proximal arm is connected to the distal end of the proximal sleeve, and the free end of each proximal arm extends in the direction of the central axis beyond that distal end of the proximal sleeve;

the method comprising:
- a step of positioning the distal arms in the atrial cavity,
- a step of deploying the distal arms in the atrial cavity,
- a step of pressing the distal arms against the atrial face of the leaflets,
- a step of moving the proximal sleeve towards the leaflets, with proximal arms deployed so that the proximal arms define a receiving space for the leaflets, so as to insert the leaflets in the receiving space, and pressing the proximal arms against the ventricular face of the leaflets by applying an axial force towards said leaflets,
- a step of deploying the distal sleeve and the proximal sleeve, and assembling the distal sleeve with the proximal sleeve so as to form the tubular frame.

Optionally, the method uses a tool for deploying the implant, the implant being mounted in its contracted configuration in the tool, the tool including:
- an inner sheath for retaining the distal sleeve in a contracted configuration, and for retaining each distal arm in an axial configuration, and
- another sheath for retaining the proximal sleeve in a contracted configuration, and for pressing each proximal arm against the other sheath, the method comprising:
- a step of deploying the proximal arms, by retracting the other sheath so as to release the proximal arms,
- the step of positioning the distal arms in the atrial cavity, with the inner sheath still positioned around the distal arms,
- the step of deploying the distal arms in the atrial cavity, by retracting the inner sheath so as to release these distal arms,
- the step of pressing the distal arms against the atrial face of the leaflets, by moving the tool toward the ventricular cavity so as to apply an axial force towards the ventricular cavity,
- the step of moving the proximal sleeve towards the leaflets, with the other sheath still covering the proximal sleeve, and pressing the proximal arms against the ventricular face of the leaflets so as to apply an axial force towards the atrial cavity,
- the step of deploying the distal sleeve and the proximal sleeve, by retracting the inner sheath and the other sheath.

Optionally:
- the step of positioning the distal arms in the atrial cavity follows the step of deploying the proximal arms,
- the step of deploying the distal arms in the atrial cavity follows the step of positioning the distal arms in the atrial cavity,
- the step of pressing the distal arms against the atrial face of the leaflets follows the step of deploying the distal arms in the atrial cavity,
- the step of moving the proximal sleeve towards the leaflets follows the step of pressing the distal arms against the atrial face of the leaflets, and
- the step of deploying the distal sleeve and the proximal sleeve follows the step of moving the proximal sleeve towards the leaflets.

Optionally:
said other sheath, and the proximal sleeve in the contracted configuration within the other sheath, are introduced in the ventricular cavity from a first way,
the inner sheath, and the distal sleeve in the contracted configuration within the inner sheath, are introduced in the atrial cavity, from a second way different from said first way.

The native valve is chosen between a mitral valve or a tricuspid valve.

The invention will be better understood upon reading the following description, provided solely as an example, and done in reference to the appended drawings, in which:

FIG. 7 is a view of a treatment device, in which the implant of FIG. 1 is loaded in a contracted configuration;

FIGS. 8 to 11 illustrate different deployment phases of the implant of FIG. 1 in an atrio-ventricular passage;

Figure 3:
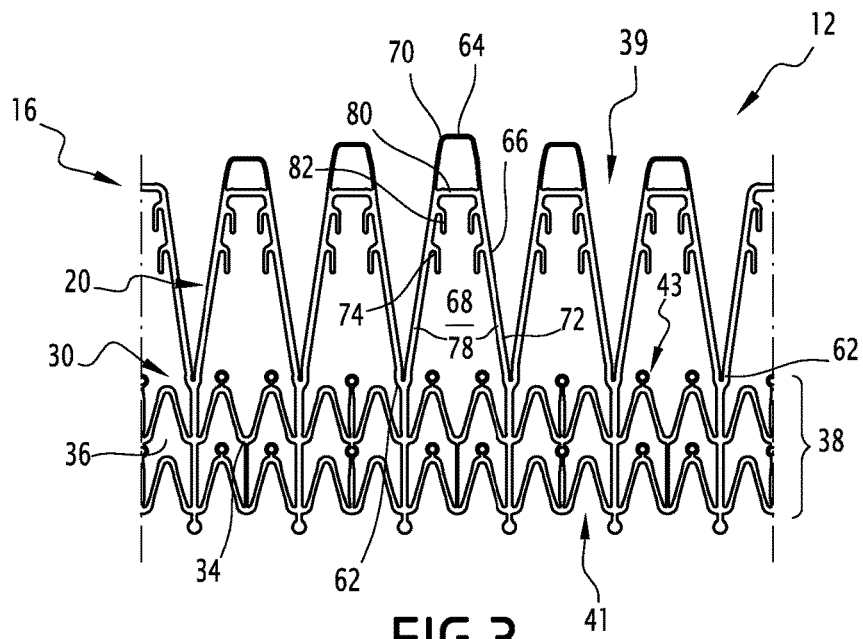
FIG. 3 is a developed view of the lower part of the implant of FIG. 1 in the deployed configuration of the implant.
Figure 4:
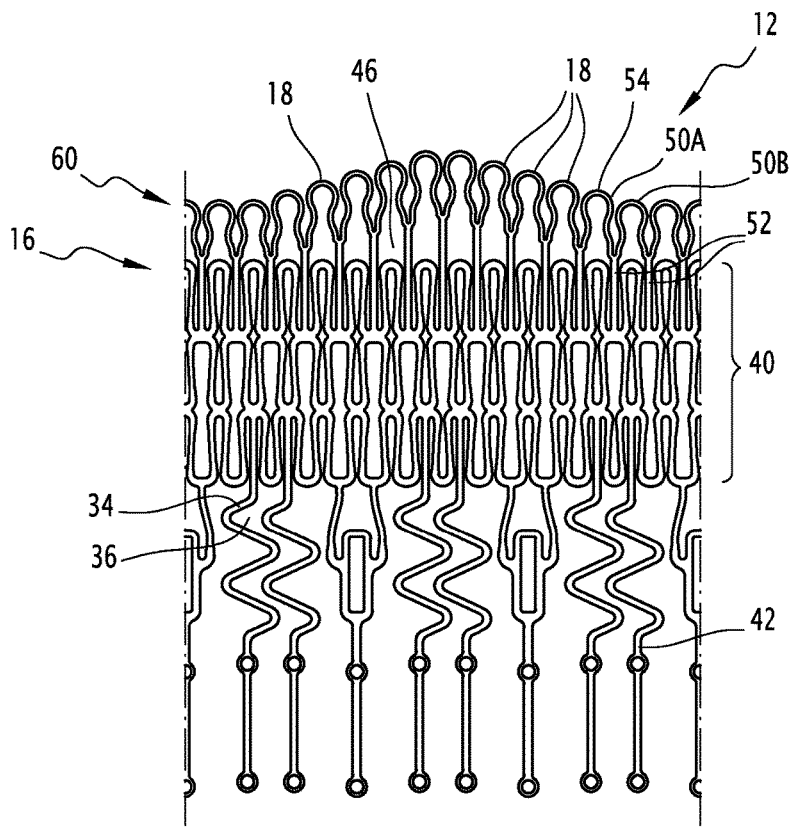
FIG. 4 is a view similar to FIG. 3 of an upper part of the implant in the contracted configuration of the implant.
Figure 16:
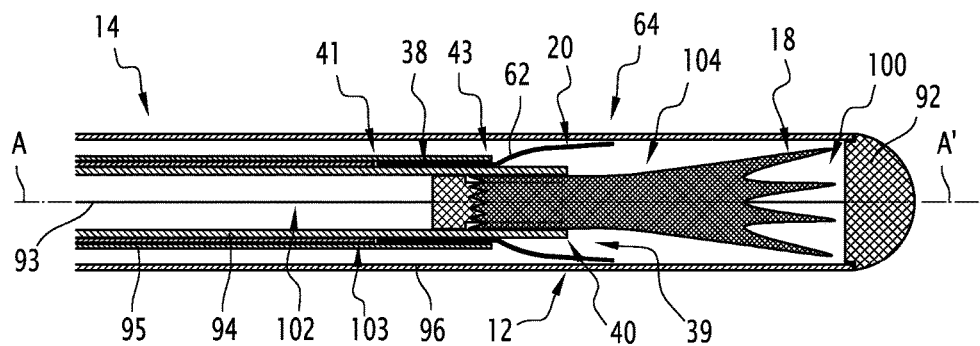
Figure 23:
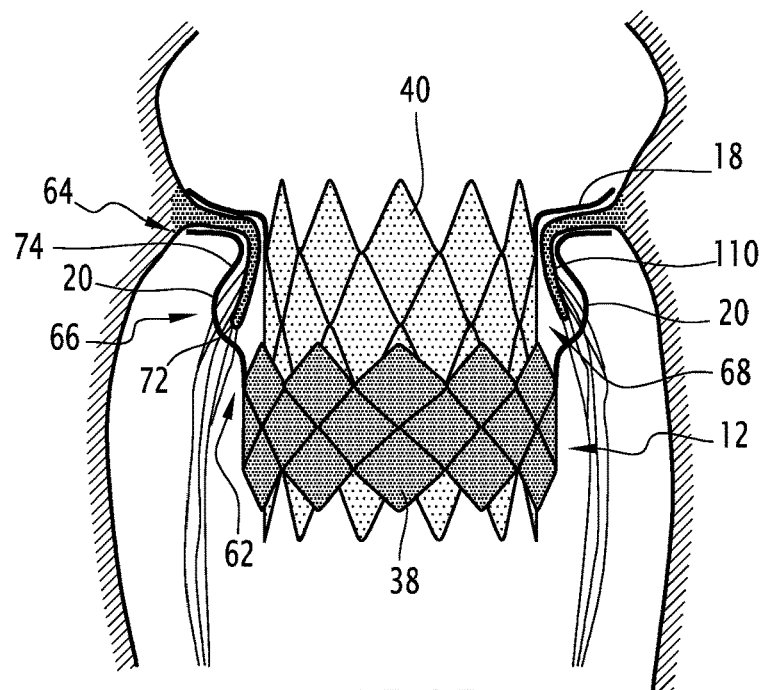
Figure 27:
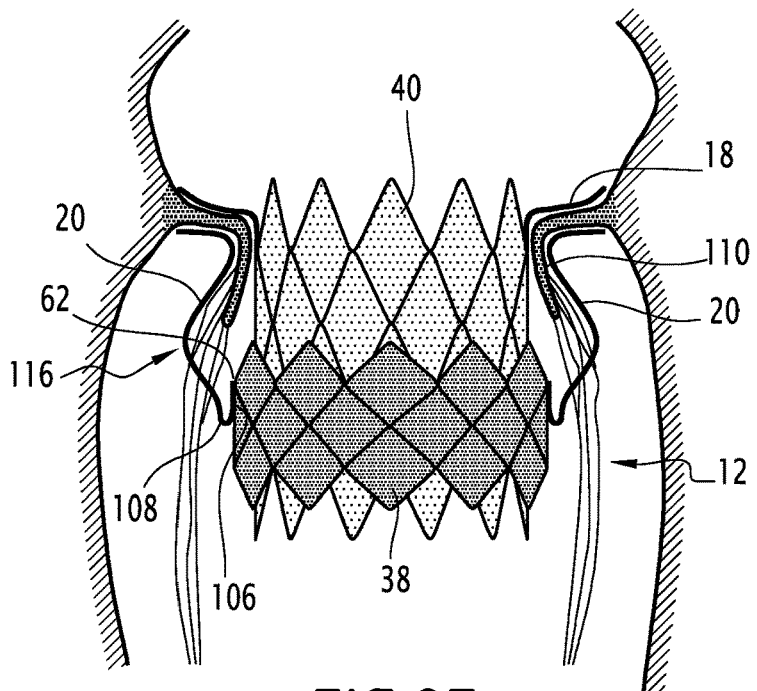
Figure 24:
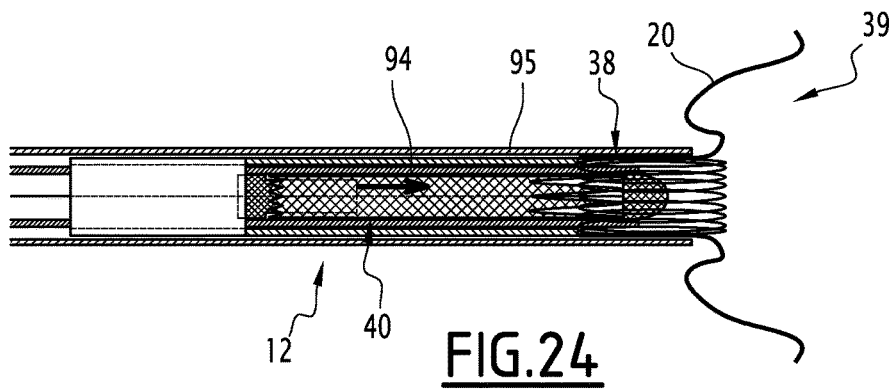
Figure 25:
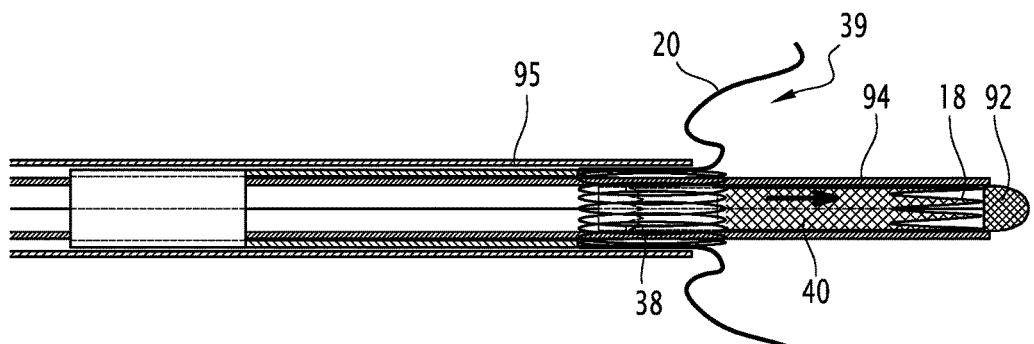
Figure 26:
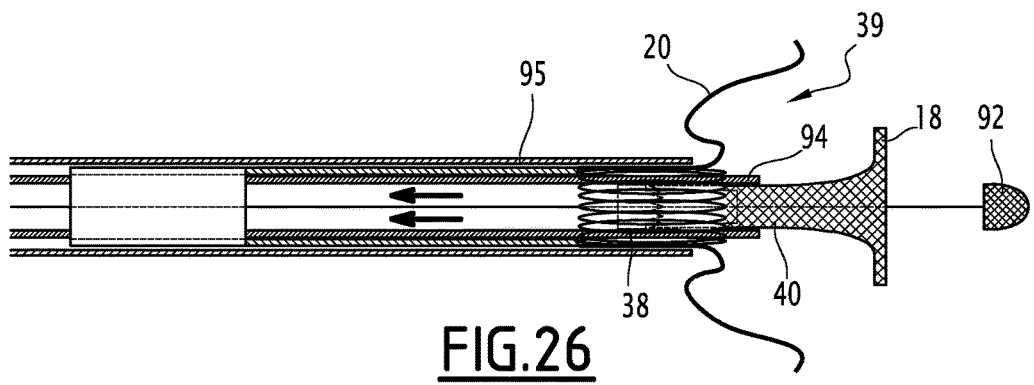
Figure 28:
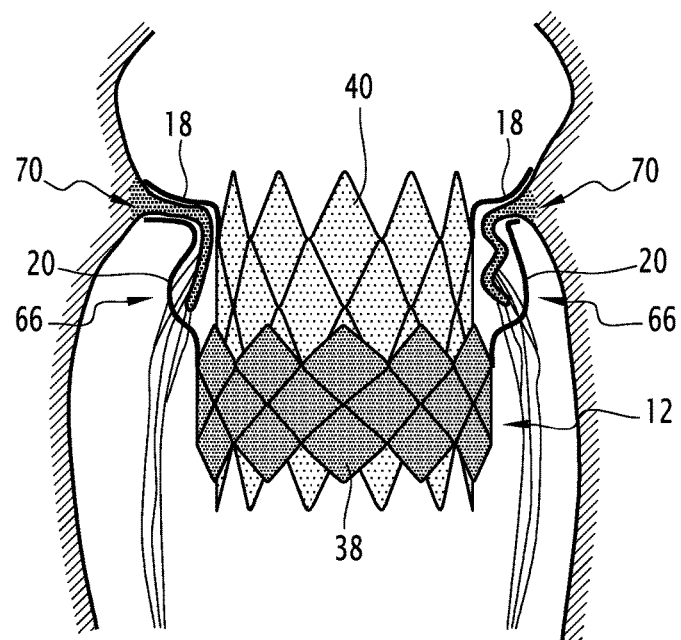
Figure 29:
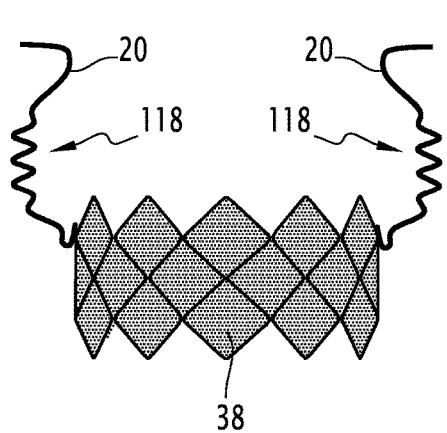
Figure 30:
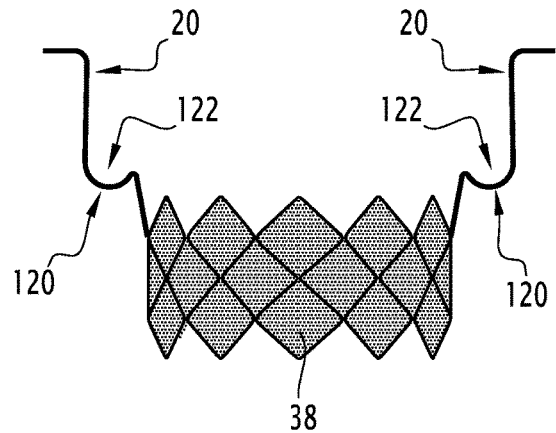
Figure 31:
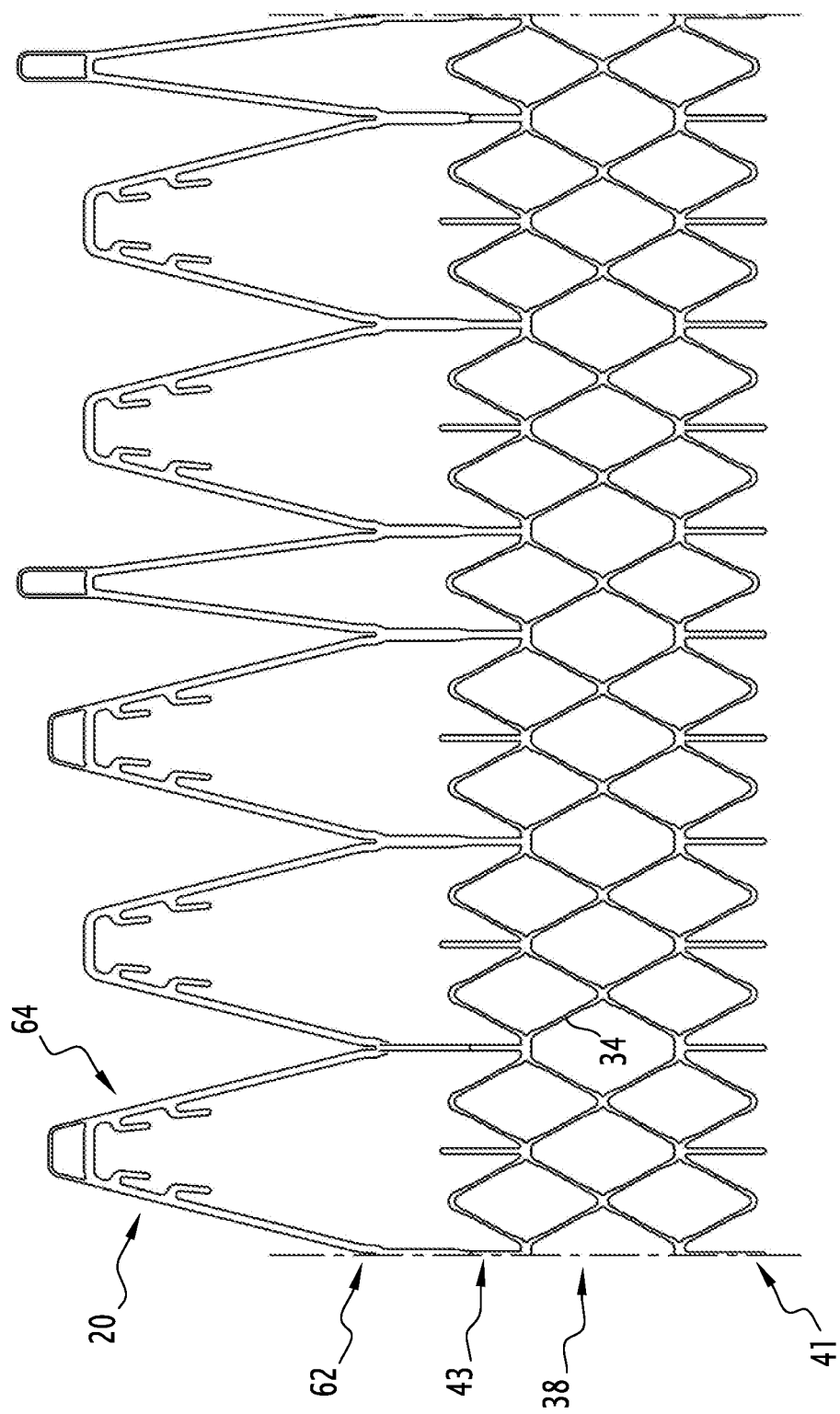
Figure 32:
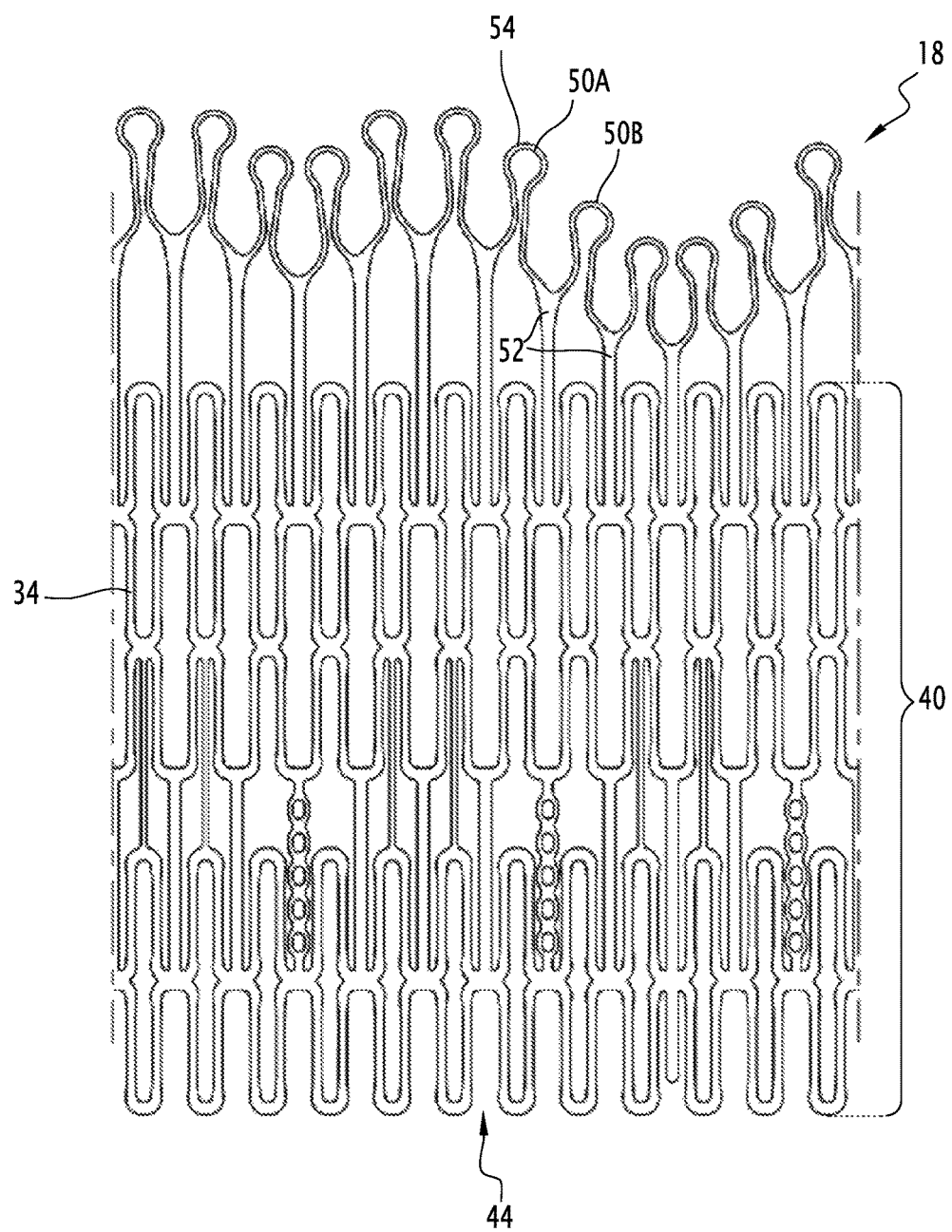

FIG. 16 diagrammatically shows, in axial cross-section, a treatment device according to another alternative embodiment, in which the implant is loaded in a contracted configuration;

FIGS. 17 to 22 are diagrammatic views similar to FIG. 16, showing the treatment device of FIG. 16 in different deployment phases;

FIG. 23 is a diagrammatic profile view of an implant according to one alternative embodiment of that of FIGS. 3 and 4, positioned in a blood flow passage;

FIGS. 24 to 26 are diagrammatic views similar FIGS. 16 to 22, showing the treatment device comprising the implant of FIG. 23, in different deployment phases of that implant;

FIGS. 27 and 28 are diagrammatic views similar to FIG. 23, showing the implants according to respective alternative embodiments, positioned in a blood flow passage;

FIGS. 29 and 30 are diagrammatic profile views of a first part of an implant according to respective alternative embodiments;

FIGS. 31 and 32 are views similar to FIGS. 3 and 4, respectively showing a first part and a second part of the implant according to another alternative embodiment;

FIGS. 33 to 38 are diagrammatic profile views of an implant during different deployment phases of a method for placing the implant according to a second embodiment; and FIGS. 39 to 44 are diagrammatic profile views of an implant during different deployment phases of a method for placing the implant according to a third embodiment.

A first treatment device 10 according to the invention is illustrated by FIG. 7.

The device 10 includes an implant 12, shown in detail in FIGS. 1 to 6, and a tool 14 for deploying the implant 12 designed to position and deploy the implant 12 in a blood flow passage, for example a passage situated in the heart of a patient.

The implant 12 is advantageously an endovalve, in particular a heart valve designed to replace a defective native valve. The endovalve is advantageously an atrio-ventricular valve, designed to replace the native mitral valve situated between the left atrium and left ventricle, so as to allow a one-way flow of the blood flow between the atrial cavity and the left ventricular volume.

Alternatively, the endovalve is an atrio-ventricular valve designed to replace the heart valve in the tricuspid position, thus the native valve is for instance a tricuspid valve. In this case, it should be noticed that the implant may be brought towards the tricuspid valve through a ventricular way, or in a variant through the right jugular vein.

Figure 1:
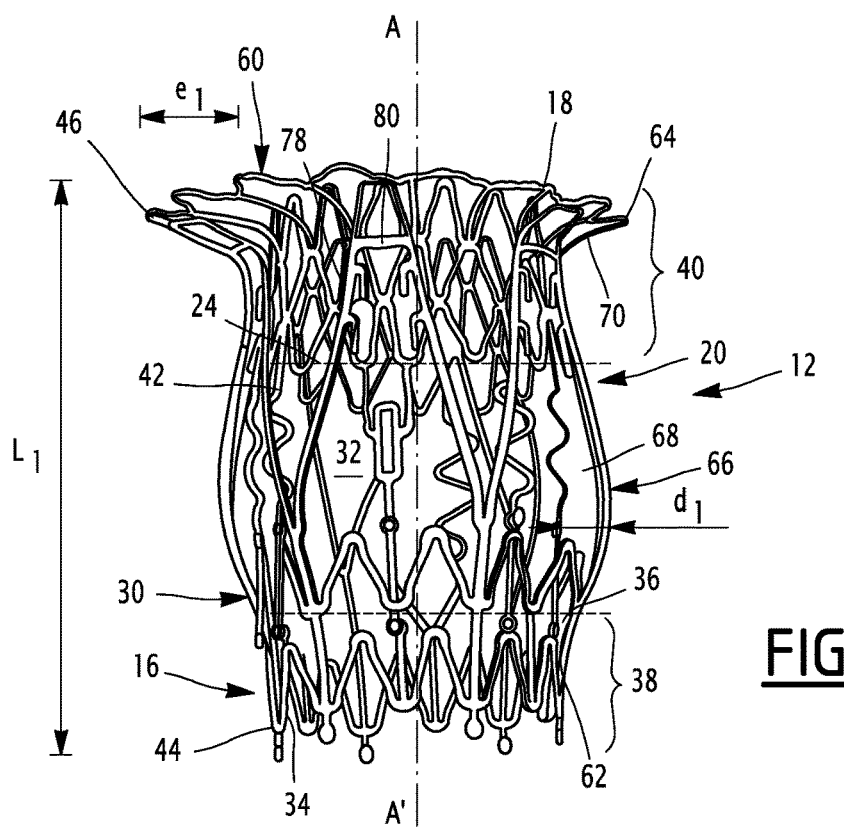
FIG. 1 is a side view of a first implant according to the invention, in a deployed configuration.
Figure 2:
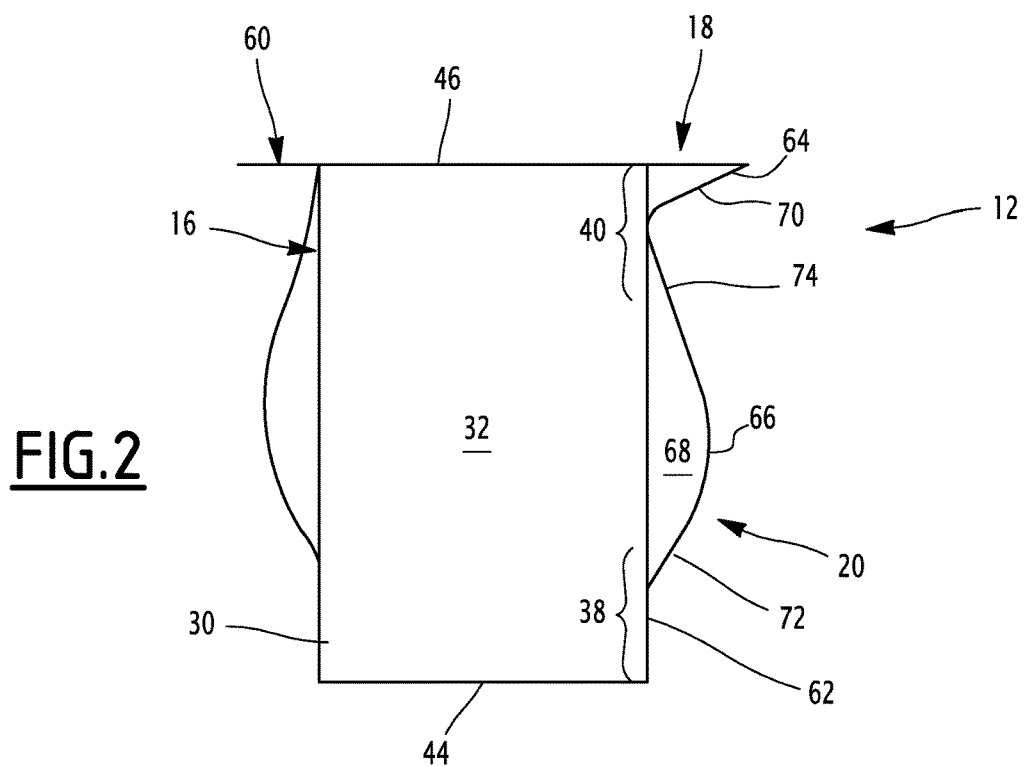
FIG. 2 is a diagrammatic view, in partial cross-section along a median axial plane, of the implant of FIG. 1.

As illustrated by FIGS. 1 and 2, the implant 12 includes a tubular frame 16, a plurality of distal arms 18 designed to form a distal pressing on a distal face of a valve leaflet, and a plurality of proximal arms 20 designed to receive a proximal face of the leaflets of the native valve to attach on that valve.

In the case where the native valve is the mitral valve, the distal face makes up the atrial face and the proximal face makes up the ventricular face.

The implant 12 further advantageously includes a closing member 24 with a base of a tissue, in particular synthetic or natural tissue, such as bovine, equine and/or porcine pericardium. The closing member 24 is shown diagrammatically in dotted lines in FIG. 2. It is designed to ensure the one-way flow of blood through the implant 12.

The implant 12 generally extends along a central axis A-A'. It can be deployed between a contracted configuration, which it occupies when it is positioned in the deployment tool 14, and a deployed configuration, which it occupies when it is situated outside the deployment tool 14.

In one advantageous alternative, the implant 12 is self-expandable, i.e., its deployed configuration constitutes its idle position, the implant 12 in its contracted configuration being biased toward its deployed configuration.

The frame 16, the arms 18 and the arms 20 are for example formed from a stainless steel with elastic properties. Alternatively, these elements are formed with a base of shape memory metal such as Nitinol or a flexible polymer fiber.

The tubular frame 16 is formed by a tubular body 30 inwardly defining a blood flow conduit 32.

The body 30 is advantageously made with a base of a plurality of filiform elements 34 or a single piece forming a peripheral wall with axis A-A' and delimiting passage openings 36 between them.

The body 30 comprises a first part 38, also called proximal sleeve, and a second part 40, also called distal sleeve 40. It should be noticed that since the body 30 is made of the first part 38 and the second part 40, this body 30 can be considered as established only when said first 38 and second 40 parts are assembled together.

In the example illustrated in FIGS. 3 and 4, the proximal sleeve 38 is made up of undulating filiform elements 34, and the distal sleeve 40 is formed by undulating filiform elements 34. A plurality of longitudinal members 42 connect the proximal sleeve 38 to the distal sleeve 40.

Each sleeve 38, 40 comprises a plurality of rows of undulating filiform elements 34 connected to each other by longitudinal tabs.

Alternatively, the frame 16 is formed by a mesh of interlaced threads for example delimiting polygonal meshes.

In this example, the proximal sleeve 38 and the proximal arms 20 form a first integral assembly, shown in FIG. 3. This assembly is attached on a second integral assembly shown in FIG. 4, and formed by the members 42, the distal sleeve 40 and the distal arms 18.

The first assembly and the second assembly are attached one on top of the other, then optionally secured using sutures or another connecting means.

Advantageously, when the proximal sleeve 38 is separated from the distal sleeve 40, and when no outside bias is present, said proximal sleeve has a diameter smaller than that of the distal sleeve 40 when no outside bias is present. Thus, when the distal sleeve 40 is deployed inside the proximal sleeve 38, it exerts a radial force on an inner surface of that proximal sleeve 38, that radial force being sufficient to provide the connection between the proximal sleeve 38 and the distal sleeve 40.

To that end, it will be noted that the distal sleeve 40 is for example made from stainless steel with elastic properties. For example, the distal sleeve 40 is deployed by inflating an inflatable balloon.

Alternatively, the distal sleeve 40 may be made from a shape memory metal, such as nitinol (Nickel/Titanium).

Furthermore, the distal sleeve 40 has a length, in the direction of the axis A-A', greater than the length of the proximal sleeve 38. Thus, the proximal sleeve 38 can be positioned in different positions on the distal sleeve 40, in particular depending on the predetermined configuration of the blood flow passage designed to receive the implant 12.

As in particular shown in FIG. 3, the proximal sleeve 38 extends longitudinally between a proximal end 41 and a distal end 43 of the sleeve. Each proximal arm 20 extends between an end 62 connected to the distal end 43 of the proximal sleeve 38, and a free end 64. Thus, each proximal end 20 extends in the direction of the central axis A-A' beyond that distal end 43 of the proximal sleeve 38.

Such a configuration in particular makes it possible to facilitate the insertion of the valve leaflets into a receiving space 39 of those valve leaflets delimited between the proximal arms 20, as will be described later in reference to FIGS. 16 to 22 and 24 to 26.

In particular, it will be noted that the proximal sleeve 38 extends completely outside that receiving space 39, with the result that it does not hinder the insertion of the valve leaflets in the receiving space 39.

The transverse section of the tubular frame 16 and that of the conduit 32 is advantageously substantially constant.

The conduit 32 extends through the frame 16 along the axis A-A'. It emerges axially at a proximal end 44 of the frame 16 and a distal end 46 of the frame 16. It will be noted that the proximal end 44 of the frame 16 may be formed by the proximal end 41 of the proximal sleeve 38, or by the proximal end of the distal sleeve 40, based on the relative arrangement of those proximal 38 and distal 40 sleeves. Furthermore, the distal end 46 of the frame 16 is generally formed by the distal end of the distal sleeve 40.

In the contracted configuration, the section of the conduit 32 is minimal. The length L1 of the tubular frame 16, considered along the axis A-A' between its ends 44, 46, is then maximal. On the contrary, in the deployed configuration, the length L1 of the tubular frame 16 is minimal and the transverse section of the conduit 32 is maximal.

In the deployed configuration, the length L1 of the frame 16, considered between its ends 44, 46 along the axis A-A', is greater than 10 mm and is in particular comprised between 5 mm and 45 mm to adapt to a variety of anatomical configurations.

As illustrated by FIGS. 1, 2 and 4, the distal arms 18 extend radially from the tubular frame 16 in the vicinity of the distal end 46, for example at a distance of less than 10% of the length L1 of the frame relative to the distal end 46.

The distal arms 18 are distributed at the periphery of the frame 16. The number of distal arms is greater than 2, and is in particular comprised between 5 and 20.

In the example illustrated in FIG. 4, the arms 18 extend continuously over the entire periphery of the tubular frame 16 around the axis A-A' while being adjacent to one another.

Each distal arm 18 is formed by a loop 50A, 50B having two inner segments 52 shared with an adjacent distal arm 18, and one unique outer segment 54 folded in a loop.

As illustrated by FIGS. 1 and 4, the distal arms 18 are movable between an axial position, shown in FIG. 4, when the implant 12 is in its contracted configuration, and a transverse position, shown in FIG. 1, when the implant 12 is in its deployed configuration.

In the transverse position, when idle, without any outside bias, each distal arm 18 extends perpendicular to the axis A-A'.

In that position, the expanse e1 of each distal arm 18, taken between the frame 16 and the free end of the arm 18, perpendicular to the axis A-A', is smaller than 50% of the length L1.

Alternatively, the expanse e1 of the distal arms 18 may be even larger, in particular greater than 50% of the diameter of the tubular frame 16. Such an expanse makes it possible to overflow beyond the mitral annulus and press on the walls of the left atrium.

Advantageously, each of the distal arms 18 may include a distal region, more flexible than a proximal region forming a slightly concave tab. The concave side is then oriented toward the left atrium and the tab is pressed beyond the mitral annulus on the walls of the left atrium. In this configuration, each distal arm 18 advantageously has a radial expanse greater than 80% of the length L1 of the frame 16.

Figure 6:
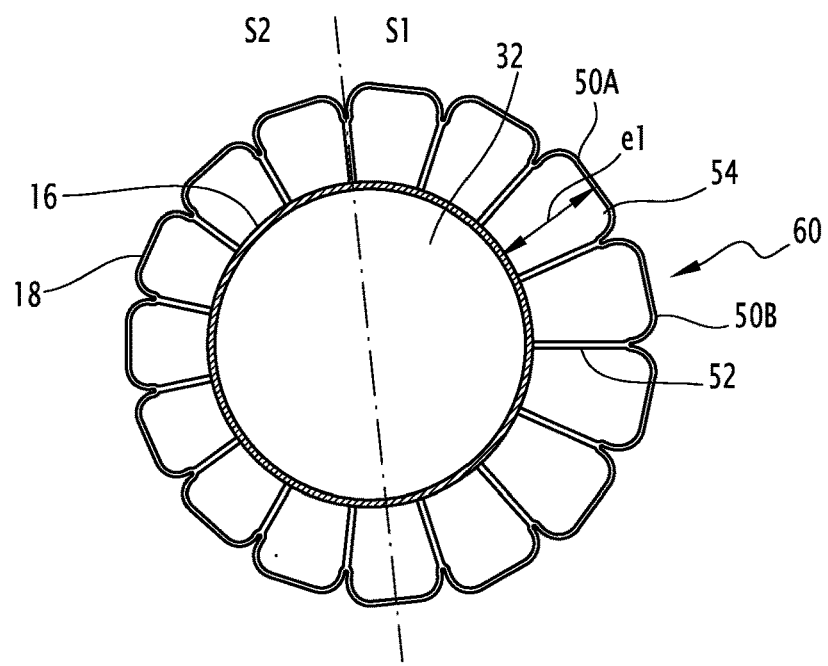
FIG. 6 is a top view of the implant shown in FIG. 1, illustrating the distal collar.

As illustrated by FIG. 6, the radial expanse e1 of the arm 18 in a first angular sector S1 is also larger than the radial expanse e1 of the arms 18 situated in the second angular sector S2. This makes it possible to adapt to the anatomical configuration of the seat of the mitral valve, in particular when the native valve is the mitral valve.

In the deployed configuration, the distal arms 18 thus form a continuous annular collar 60 designed to press on the distal incline of the native valve, on the atrial incline, on the annulus and on the wall of the atrium when the native valve is mitral valve.

Advantageously, a skirt made from tissue, in particular Dacron or another synthetic biological tissue, covers the collar 60. This skirt thus provides sealing between the left atrium and the left ventricle at the perimeter of the tubular frame 16. The skirt is advantageously sewn on the distal arms 18 and may optionally radially overflow past the collar 60 to press on the atrial face of the mitral annulus and on the inner faces of the walls of the left atrium.

The skirt may also cover the inner surface of the frame 16 as far as the closing member 24 to guarantee the passage of blood through the closing member 24 without any risk of leak through the wall of the frame 16.

In the example shown in the Figures, the implant 12 includes a plurality of proximal arms 20 angularly spaced apart from one another around the axis A-A'.

The number of proximal arms 20 is smaller than or equal to the number of distal arms 18. In this example, the number of proximal arms 10 is greater than 2, and is in particular comprised between 4 and 10.

Each proximal arm 20 extends axially between an end 62 connected to the frame 16, situated in the vicinity of the proximal end 44, and a free end 64 designed to press against a distal arm 16 or against the frame 16 when the implant 12 is in its deployed configuration.

The distance separating the proximal end 44 of the frame 16 from the connected end 62 along the axis A-A' is smaller than 20% of the length L1 of the frame 16.

Each proximal arm 20 thus has a length, considered parallel to the axis A-A, along the frame 16, greater than 50%, advantageously greater than 70% of the length L1 of the tubular frame 16, considered between the proximal end and the distal end.

Figure 5:
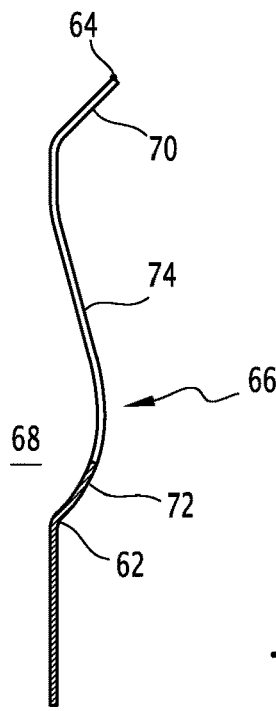
FIG. 5 is a side view illustrating the side profile of the side proximal arms.

As illustrated by FIG. 5, each proximal end 20 includes, between its connected end 62 and its free end 64, at least one intermediate region 66 extending along and radially away from the frame 16 to define a longitudinal cavity 68 for receiving a valve leaflet.

Advantageously, at least one proximal arm 20 further includes a distal region 70 forming an outer tab pressed below a distal arm 18, or on the frame 16.

As illustrated by FIGS. 1 and 5, at least one arm 20 thus has an S-shaped profile with an outwardly curved intermediate profile 66 relative to the axis A-A' and a distal region 70 protruding radially away from the axis A-A' relative to the intermediate region 66.

As illustrated by FIGS. 1 and 5, the intermediate region 66 comprises a proximal segment 72 diverging radially away from the axis A-A extending from the connected end 62, and a distal segment 74 converging toward the axis A-A' while moving along the axis A-A' from the connected end 62 toward the free end 64.

The maximum distance d1 radially separating the intermediate region 66 of the outer enclosure from the tubular frame 16 is greater than 10% of the diameter of the tubular frame. That distance is advantageously smaller than 40% of the diameter of the tubular frame 16.

The distal region 70 forms a tab that converges radially outward from the converging segment 74.

In the deployed configuration of the implant 12, each distal region 70 protrudes radially below a distal arm 18.

The distal region 70 has a flexibility in flexure greater than that of the intermediate region 66. The filiform element making up the distal region 70 for example has a maximum thickness smaller than the maximum thickness of the filiform element forming the intermediate region 66.

The maximum radial expanse of the distal region 70, considered between the end of the distal segment 74 and the free end 64 of the distal region 70, is greater than the radial expanse of the intermediate region 66.

Furthermore, the proximal arms 20 situated in the first angular sector S1 include a distal region 70 with a radial expanse greater than the radial expanse of the distal regions 70 of the proximal arms 20 situated in the second angular sector S2, connected with the length of the distal arms 18.

According to the invention, in the deployed configuration of the implant 12, each proximal arm 20 is radially deformable, between a radially contracted idle position and a position radially separated from the idle position, for the insertion of the leaflets of the native valve into the cavity 68.

In the idle position, each proximal arm 20 is pressed against the frame 16 and/or against a distal arm 18 without any outside bias.

In the deployed position, each arm 20 is elastically returned toward its idle position, the idle position constituting its stable position.

The length of the converging segment 74, considered along the axis A-A', is greater than the length of the diverging segment 72. The length of the distal region 70 is smaller than the length of the converging segment 74 and the length of the diverging segment 72.

In the example shown in FIGS. 1 and 3, each arm 20 is formed by linear branches 78 forming an upside down V converging distally. A transverse end segment 80 connects the branches 78 to each other. The distal region 70, when it is present, protrudes from the end segment 80.

The branches 78 of two adjacent proximal arms 20 are in contact with one another at their connected ends 62.

The maximum angle formed by the branches 78 is for example smaller than 45°, and is in particular smaller than 30°.

In the example shown in the Figures, each proximal arm 20 is further provided with anchoring elements 82 in a valve leaflet each formed by an apex protruding toward the proximal end 44.

Traditionally, the closing member 24 is formed by flexible flaps (not shown) fixed on the frame 16 in the conduit 32. Each flap is for example formed by a polymer film or a layer of organic film such as the pericardium of an animal, in particular calf pericardium. The flaps are deformable in a closing position, in which the blood flow from the proximal end toward the distal end is prevented, and a blood flow passage position, in which the flaps are separated from each other.

The flaps are partially fixed on the frame 16 along a suture line. The distal edge of the flaps is situated axially away from the distal edge of the frame. The distance axially separating the distal edge of the frame 16 from the distal edge of the flaps is for example greater than 10%, in particular substantially equal to 20% of the length L1.

As illustrated by FIG. 7, the deployment tool 14 for the first device 10 includes an inner rod 90 provided with a head 92 for maintaining one end of the implant 12, a stent 93 mounted coaxially slidably on the rod 90, an inner sheath 94 mounted slidably relative to the stent 93 and an outer sheath 96 mounted slidably around the inner sheath 94, along an insertion axis B-B'.

The stent 93 and the sheath 94, 96 are slidably movable along the axis B-B', independently of one another, and relative to the rod 90.

Locking members (not shown) are provided between the rod and the stent 93, between the stent 93 and the sheath 94, 96 to avoid spontaneous sliding of the stent 93, the outer 96 and inner 94 sheaths. This makes it possible to proceed by successive steps with the removal of the outer sheath 96, removal of the inner sheath 94, and the release of the proximal end 44. The inner stent 93 includes an axial locking stop 98 extending across from the head 92. The stop 98 is designed to lock the distal end 46 of the implant 12.

The head 92 delimits a housing 100 for receiving the proximal end 44 of the implant 12, in which the proximal end 44 is kept radially compressed. This end 44 is also axially fixed relative to the stent 93.

The stent 93 and the inner sheath 94 delimit an inner annular space 102 designed to receive the frame 16 and the distal arms 18. The outer sheath 96 delimits an outer annular space 104 designed to receive the proximal arms 20.

The stent 93 is provided with at least one angular indexing stop 105A, 105B for the implant 12 to angularly fix the implant 12 relative to the stent 90 in the inner sheath 94 around the axis of the stent 90. The or each indexing stop 105A, 105B is advantageously radiopaque to identify the arrangement of atrial arms 20 with unequal sizes.

Thus, in the example shown in FIG. 7, the stent 93 includes two diametrically opposite stops 105A, 105B axially offset along the axis B-B'.

The stop 105A situated furthest from the head 92 is designed to receive the proximal arms 18 with the largest expanse e1, while the stop 105B situated closest to the head is designed to receive the proximal arms 18 with the smallest expanse e1. The operator of the device can thus orient the implant during its placement in the blood flow passage.

It is thus possible to place the longest distal arms 18 in the posterior area of the mitral annulus when the implant 12 is designed to replace the mitral valve.

In the contracted configuration, when the implant 12 is received in the deployment tool 14, the length of the frame 16 is maximal, and its outer diameter is minimal. The distal arms 18 then occupy their axial position, substantially parallel to the axis A-A'.

The proximal arms 20 are pressed axially along the axis A-A'. The outer diameter of the implant 12 is then minimal.

In this configuration, the frame 16 is received in the inner annular space 102 separating the stent 93 from the inner sheath 94. It is kept in position by the sheath 94. The distal arms 18 are placed in contact with the stop 98, or in the vicinity thereof in the axial position.

The proximal arms 20 are pressed against the inner sheath 94 in the outer annular space 104. The proximal end 44 of the frame 16 protrudes in the housing 100 of the head 92 and is axially fixed relative to the stent 93. The head 92 and the rod 50 are axially locked relative to the stent 93, the head 92 being close to the stop 98.

When the implant 12 must be positioned, in particular to replace a native valve, it is inserted between the leaflets 110 of the native valve around the seat 112 of the valve, as shown in FIG. 8. This insertion may be done, using the device of FIG. 7, through the transatrial approach, passing through the left atrium.

The head 92 and the downstream part of the tool 14 are inserted into the left ventricle, beyond the leaflets 110, so that the entire length of the proximal arms 20 is positioned in the left ventricle beyond the leaflets 110 of the valve.

Then, the outer sheath 96 is retracted axially away from the head 92 relative to the inner sheath 94 and relative to the stent 93 to gradually expose the proximal arms 20.

When the arms 20 are completely exposed, the outer sheath 96 is then moved again toward the head 92 so that its free edge 114 becomes intercalated between the arms 20 and the frame 16, so as to separate the arms 20 from the contracted idle position.

The arms 20 then go into the deployed position shown in FIG. 8.

In that position, the leaflets 110 of the native valve are intercalated between the outer sheath 96, the tubular frame 16 and the proximal arms 20 to be received in the cavities 68.

Next, the tool 14 is moved toward the left atrium to press the ventricular arms 20 against the ventricular face of the leaflets 110 and anchor the apices 82 in the leaflets 110.

Figure 9:
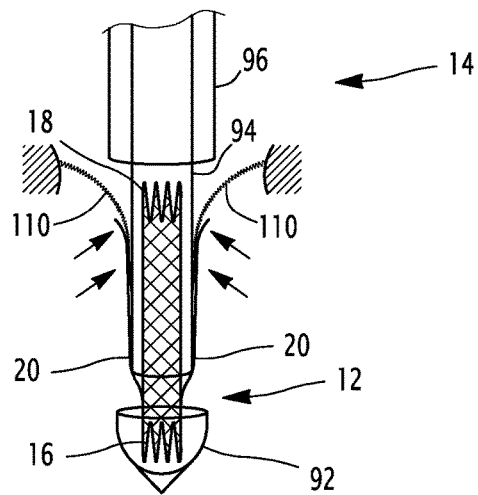

Once that is done, the sheath 96 is once again removed, as shown in FIG. 9. Under the effect of the elastic return force of the proximal arm 20 toward its idle position, the proximal arms 20 retract toward the frame 16 and thus clamp the leaflets 110 robustly.

The length of the proximal arms 20 being greater than 50% of the length of the frame 16, the leaflets 110 are maintained over a large length against the frame 16. They adopt a substantially axial configuration, parallel to the axis of the frame 16.

Then, the inner sheath 94 is retracted relative to the stent 93 to gradually expose the frame 16, then the distal arms 18.

Figure 10:
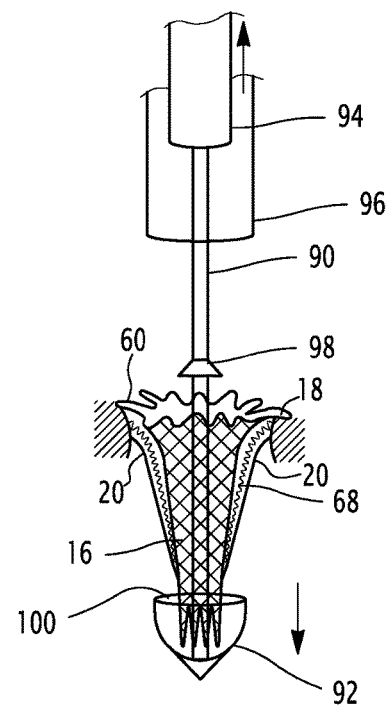

As illustrated by FIG. 10, this causes the partial radial deployment of the frame 16 and the radial deployment of the distal arms 18 toward their transverse position to bear on the atrial face of the leaflets 110.

Once this is done, the axial fastening between the stent 93 and the proximal end 44 is released by axial movement of the rod 90 and the head 92 away from the stop 98. The frame 16 is completely deployed. The stent 93 and the head 92 and the rod 91 are then removed from the patient through the inner conduit 32.

Figure 11:
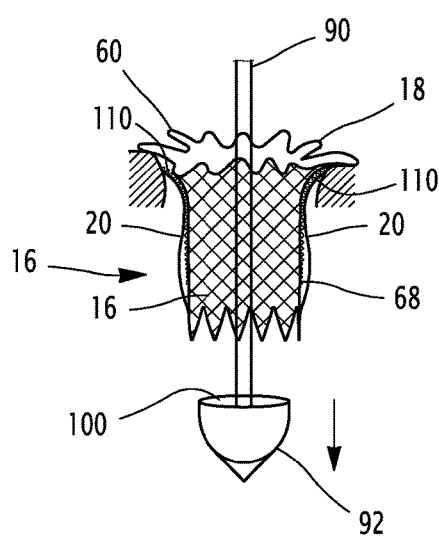

In the deployed configuration shown in FIG. 11, the distal arms 18 thus form a transverse annular collar 60 pressing robustly on the atrial face of the leaflets 110, and on the atrial face of the mitral annulus in the posterior area and optionally on the atrial wall.

The proximal arms 20 are then biased toward their idle position. The curved intermediate region 66 extending substantially away and across from the frame 16, over a substantial length of the frame 16, is perfectly configured to receive the native valve leaflet 110 and press it against the frame 16. The elastic biasing force of each proximal arm 20 toward its idle position applies robust clamping on each leaflet 110, ensuring effective and robust reception of the implant 10 in the native valve. That is the case even if the native valve has a fibrous structure and a tissue that is not very robust.

The particular axial configuration of the proximal arms 20, each defining a cavity 68 for receiving the valve leaflets over significant length relative to the length of the implant 12, and the distal closing of the cavity 68 by an annular distal collar 60 that is transverse relative to the axis A-A', contribute to ensuring robust fixing of the leaflets 110. The implant 10 is furthermore easy to implant and safe.

Advantageously, the robust fixing of the implant 12 is obtained without any radial force on the entire mitral annulus, which avoids expansion of the mitral annulus and therefore worsening of the regurgitation in light of the asymmetrical radial expanse of the distal proximal arms 18; the tubular frame 16 is implanted in an off-centered manner advantageously to press on the mitral annulus in the posterior area, which moves away from the anterior area and avoids the risk of closing of the left ventricular ejection pathway.

Each of the two native leaflets 110 is advantageously clamped on these two atrial and ventricular faces by the distal arms 18 and the proximal arms 20, respectively. Additionally, the mitral annulus is advantageously clamped in the rear area by the distal arms 18 and the proximal arms 20. This makes it possible to offset the axis of the frame 16 transversely relative to the center of the mitral annulus and to prevent the proximal part of the frame from disrupting the blood flow of the left ventricular ejection pathway.

The implant 12 essentially being fixed on the native leaflets, distal arms 18 and proximal arms 20, it is not necessary to have complete pressing on the mitral annulus, which makes it possible to eliminate the size of that annulus for implantation of the implant 12. The implant 12 then forms a reducer that has a frame diameter advantageously smaller than the diameter of the mitral annulus in which it is imported. This is equivalent to the formation of a mitral funnel, where the distal section line corresponds to the perimeter of the native mitral annulus and the proximal section line corresponds to the diameter of the tubular frame.

The blood is then guided through the closing member 24 by means of the skirt.

Figure 12:
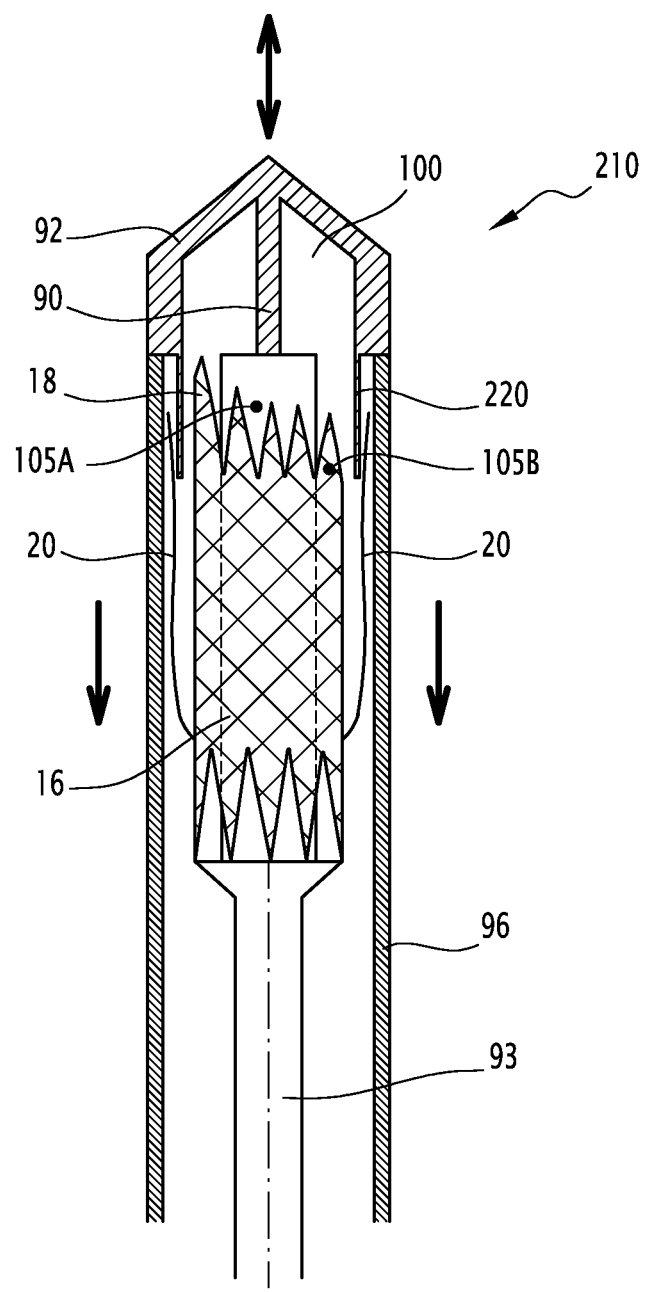
FIG. 12 is a view similar to FIG. 7 of an alternative treatment device according to the invention.

A second treatment device 210 receiving an implant 12 is illustrated by FIG. 12. Unlike the device 10 shown in FIG. 7, this device 210 is designed to be implanted through the left ventricle, then through the left atrium by the apex of the heart, in its deployed form.

In this device, the distal arms 18 are received in the housing 100 of the head 92 and are axially fixed relative to the stent 93. The device is provided with no intermediate sheath 94. An intermediate wall 220 extends from the head 92 to keep the proximal arms 20 in position and separate them from the distal arms 18.

The implant 12 contained in the device 210 is deployed from the left ventricle toward the left atrium through the native valve. Then, the outer sheath 96 is retracted to expose the proximal arms 20 as previously described. If the implant 12 is not correctly positioned, the outer sheath 96 may be moved again toward the head 98, so as to once again cover the proximal arms 20 and place those arms 20 back in the outer sheath 96.

Figure 13:
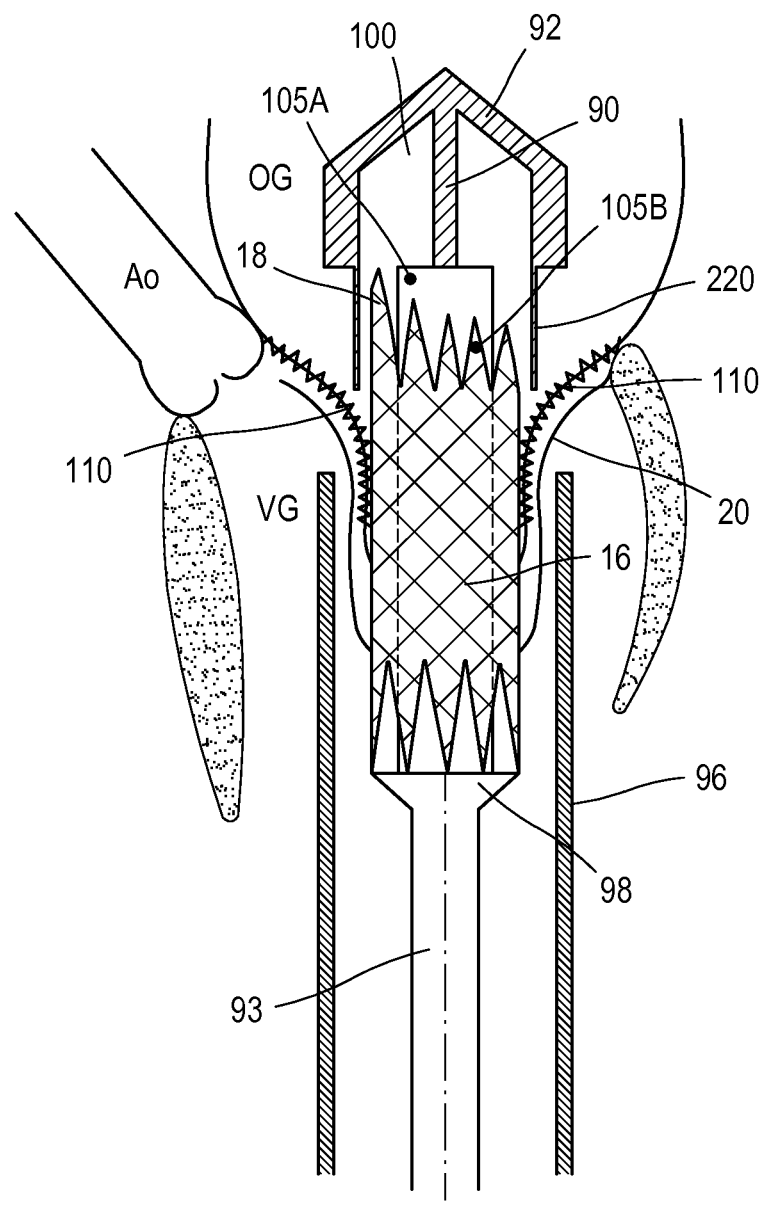
FIGS. 13 to 15 are diagrammatic views similar to FIGS. 8 to 11 illustrating different deployment phases using the device of FIG. 12.

The angular positioning of the implant 12 is obtained owing to the radiopaque stops 105A, 105B shown in FIG. 13.

The head 98 is then retracted relative to the stent 93 so that the intermediate wall 220 cooperates with the proximal arms 20 and separates them from their idle position. As illustrated by FIG. 13, the proximal arms 20 are then moved to insert the leaflets 110 into the cavities 68.

As previously specified, the axis of the frame 16 is offset relative to the center of the mitral valve, owing to the size difference between the distal arms 18.

Figure 14:
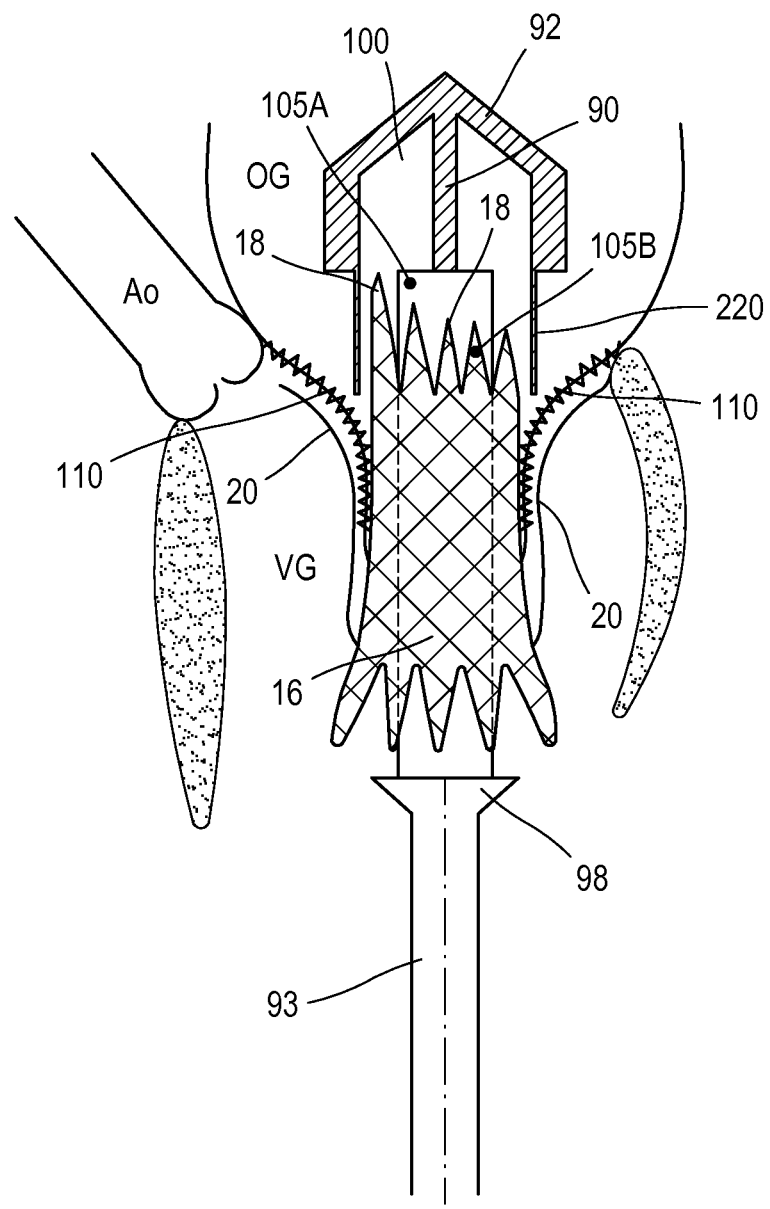
Figure 15:
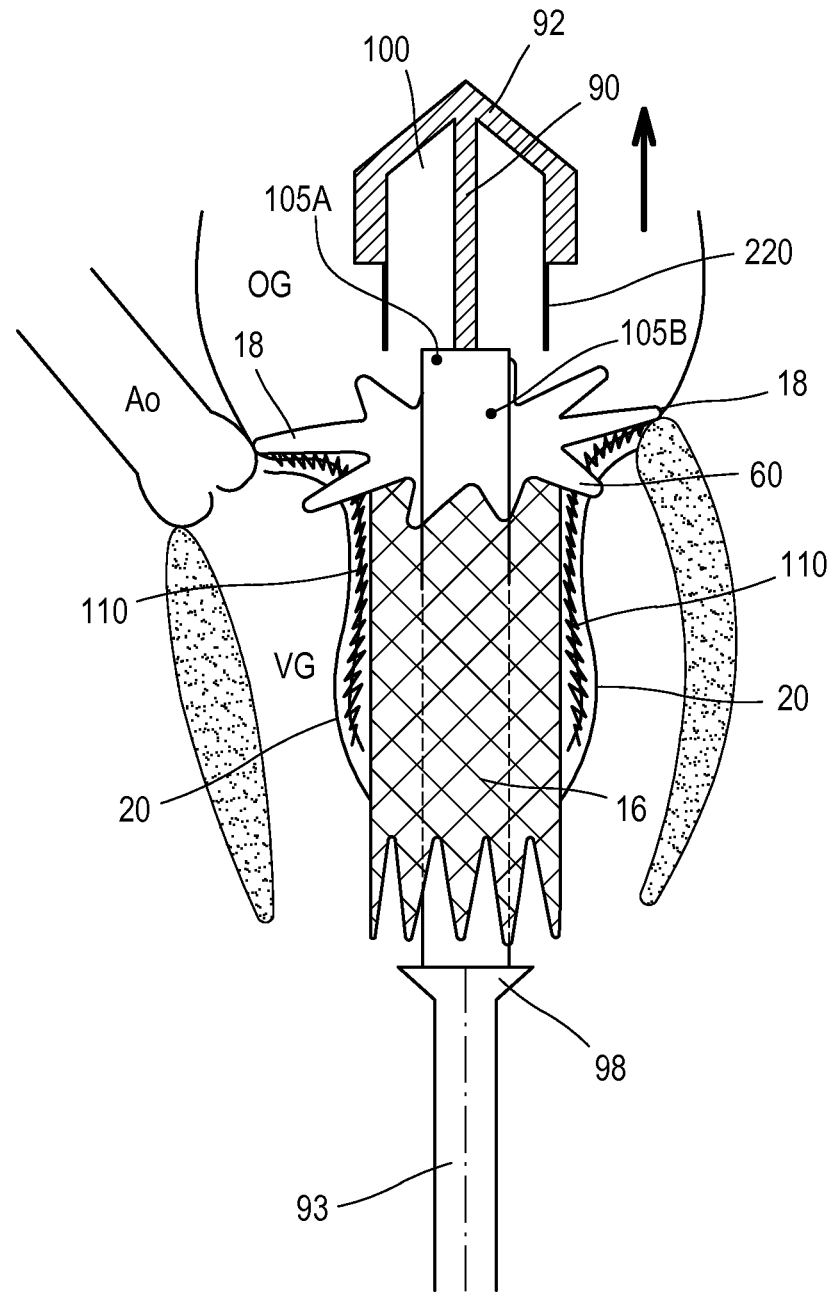

Once the proximal arms 20 are housed against the ventricular face of the leaflets 110 of the valve (FIG. 14), the head 92 is once again moved jointly with the rod 90 relative to the stent 93 toward the atrium to allow the distal arms 18 to be deployed as illustrated by FIG. 15.

Another treatment device, receiving an implant 12, is shown in FIG. 16. In this figure, and the following figures, the elements similar to those of the previous figures are designated using identical references.

As previously indicated, the implant 12 includes a first integral assembly including the proximal sleeve 38 of the frame and the proximal arms 20, and a second integral assembly including the distal sleeve 40 of the frame and the distal arms 18.

The proximal sleeve 38 extends, along the central axis A-A', between its proximal end 41 and its distal end 43. The connected end 62 of each proximal arm 20 is connected to the distal end 43 of the proximal sleeve 38, and the free end 64 of each proximal arm 20 extends in the direction of the central axis A-A' beyond that distal end 43 of the proximal sleeve 38.

As before, the deployment tool 14 for the device includes the inner rod, provided with the head 92 for maintaining one end of the implant 12, and the stent 93 mounted slidingly coaxially on the rod.

The deployment tool 14 further includes an inner sheath 94, slidably mounted relative to the stent 93, an intermediate sheath 95 slidably mounted around the inner sheath 94, and an outer sheath 96 slidingly mounted around the intermediate sheath 95.

The stent 93 and the sheaths 94, 95, 96 are slidably movable, independently of one another, and relative to the rod.

Locking members (not shown) are provided between the rod and the stent 93, between the stent 93 and the sheaths 94, 95, 96 to prevent spontaneous sliding of the stent 93, the outer 96, intermediate 95 and inner 94 sheaths. This makes it possible to proceed through successive steps with the removals of the outer sheath 96, the intermediate sheath 95 and the inner sheath 94, and the release of the proximal end.

The head 92 delimits the housing 100 for receiving the proximal end 44 of the implant 12, in which the proximal end 44 is kept radially compressed. This end 44 is also axially fixed relative to the stent 93.

The stent 93 and the inner sheath 94 delimit, between them, the inner annular space 102 designed to receive the distal sleeve 40 and the distal arms 18. Thus, the distal sleeve 40 is kept in the retracted configuration by that inner sheath 94.

The inner sheath 94 and the intermediate sheath 95 delimit, together between them, an intermediate annular sheath 103, designed to receive the proximal sleeve 38. Thus, the proximal sleeve 38 is kept in the retracted configuration by that intermediate sheath 95.

The outer sheath 96 and the intermediate sheath 95 delimit, between them, the outer annular space 104, designed to receive the proximal arms 20. Thus, each proximal arm 20 is pressed against the outer sheath 96.

When the implant 12 must be positioned, in particular to replace a native valve, it is inserted between the leaflets 110 of the native valve around the seat 112 of the valve. This insertion may be done, using the device of FIG. 16, by passing through the left ventricle, as will be described below in reference to FIGS. 17 to 22.

Figure 17:
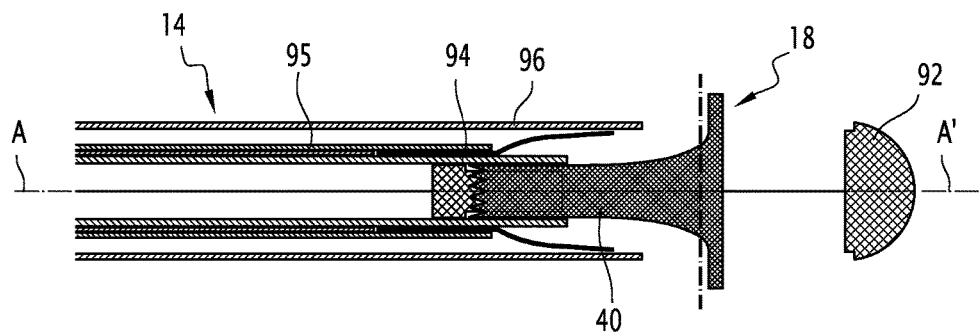

As shown in FIG. 17, the head 92 and the downstream part of the tool 14 are inserted into the atrial cavity, beyond the mitral annulus, such that the distal arms 18 are positioned in the atrial cavity beyond the mitral annulus.

The outer sheath 96 is axially retracted away from the head 92 relative to the intermediate sheath 95, the inner sheath 94 and the stent 93, to expose the distal arms 18, which are then deployed. The tool 14 is then moved toward the left ventricle to press the distal arms 18 against the atrial face of the leaflets 110.

Figure 18:
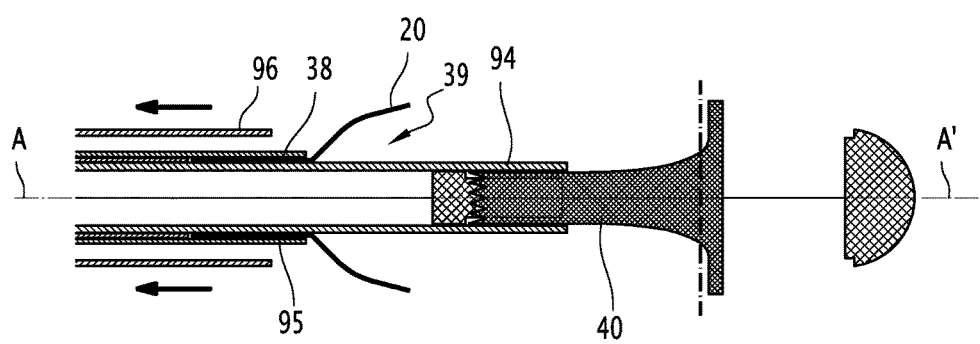

As shown in FIG. 18, the outer sheath 96 is again axially retracted to expose the proximal arms 20. The latter, which would have pressed against that outer sheath 96, are then deployed, in particular by elasticity. The separation of the proximal arms 20 is sufficient for the leaflets 110 to be found across from the receiving space 39 defined between those proximal arms 20.

Figure 19:
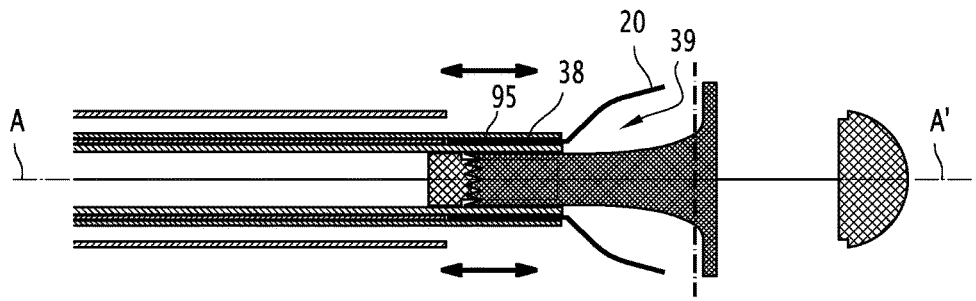
Figure 20:
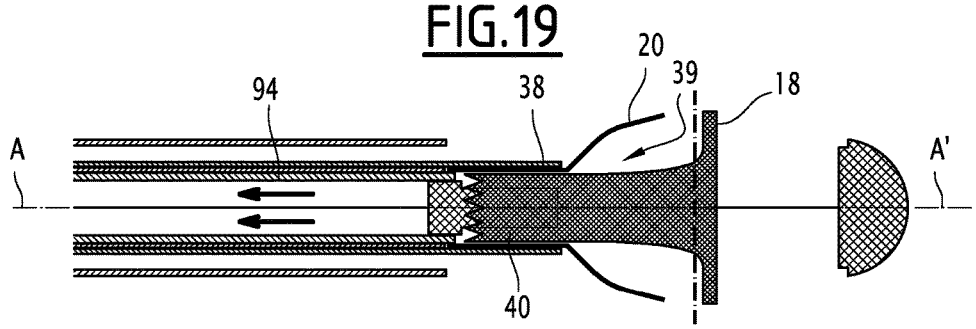

As shown in FIG. 19, it is then sufficient to move the proximal sleeve 38 and the intermediate sheath 95 surrounding it toward the leaflets 110. These leaflets 110 are thus inserted into the receiving space 39 defined between the proximal arms 20. Because the proximal arms 20 extend beyond the distal end 43 of the proximal sleeve 38, this proximal sleeve 38 does not hinder the insertion of the leaflets 110 into the receiving space 39.

Once the proximal sleeve 38 is in position, the inner sheath 94 is retracted so as to release the distal sleeve 40. This distal sleeve 40 being positioned inside the proximal sleeve 38, it is kept in the contracted configuration by that proximal sleeve 38, which in turn is kept in the contracted configuration by the intermediate sheath 95.

By deploying inside the proximal sleeve 38, the distal sleeve 40 becomes connected to that proximal sleeve 38.

It will be noted that in this position, the leaflets 110 of the native valve are intercalated between the distal sleeve 40 and the proximal arms 20.

Figure 21:
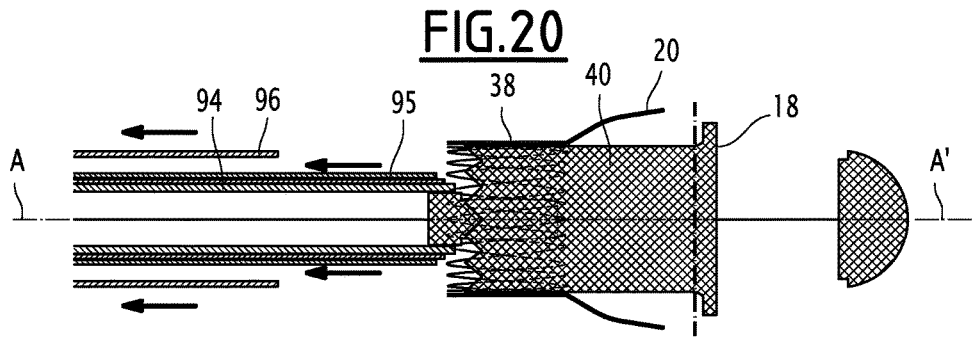

Once the proximal 38 and distal 40 sleeves are thus connected, the intermediate sheath 95 is retracted, so as to release the proximal sleeve 38, as shown in FIG. 21.

The proximal sleeve 38 then expands radially as far as its deployed configuration, as well as the distal sleeve 40 inside that deployed proximal sleeve 38.

Figure 22:
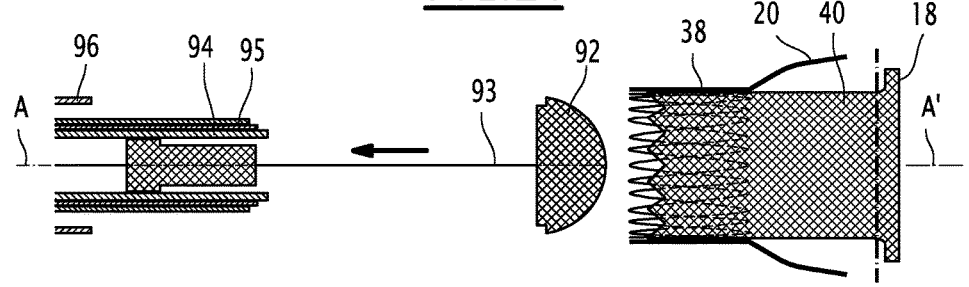

Once that is done, the axial fastening between the stent 93 and the proximal end 44 is released. The stent 93, the head 92 and the rod are then removed outside the patient through the inner conduit, as shown in FIG. 22.

It will be noted that in this deployed configuration, the distal sleeve 40 extends longitudinally, or partially inside the proximal sleeve 38, coaxially to that proximal sleeve 38, partially inside the tissue receiving space 39, such that the tissue is received between the proximal arms 20 and the distal sleeve 40, and partially beyond the tissue receiving space 39.

The implant 12 may also be inserted using another method, using a device similar to that of FIG. 16, by passing through the left ventricle, as will be described below in reference to FIGS. 24 to 26.

In these figures, the implant 12 is slightly different from that previously described, in that the shape of its proximal arms 20 is different. However, the previously described insertion method, or that which will be described now, may be used indifferently irrespective of the shape of the proximal arms 20 of the implant 12.

Furthermore, the deployment tool 14 does not necessarily include an outer sheath, but preferably only an inner sheath 94, keeping the distal sleeve 40 in the contracted position, and another sheath, which we call the intermediate sheath 95 to be consistent with the previous embodiment, keeping the proximal sleeve 38 in the contracted position.

With the exception of the shape of the proximal arms 20, which will be described later in more detail in reference to FIG. 23, and the absence of outer sheath, the deployment tool 14 and the rest of the implant 12 are similar to those described in reference to FIGS. 16 to 22.

In accordance with this other insertion method, the proximal sleeve 38 is deployed before the distal sleeve 40. Thus, as shown in FIG. 24, the intermediate sheath 95 is axially retracted so as to release the proximal arms 20, which are then deployed, in particular by elasticity. The separation of the proximal arms 20 thus defines the receiving space 39, which is then completely free.

This receiving space 39 is positioned across from the leaflets 110, such that they are inserted into the receiving space 39 by moving the deployment tool 14 toward those leaflets 110.

It is only after this that the head 92, and the inner sheath 94 containing the distal sleeve 40, are moved axially as far as the atrial cavity, beyond the mitral annulus, such that the distal arms 18 are positioned in the atrial cavity beyond the mitral annulus, as shown in FIG. 25.

Next, as shown in FIG. 26, the inner sheath 94 is axially retracted away from the head 92 to expose the distal arms 18, which are then deployed. The tool 14 is then moved toward the left ventricle to press the distal arms 18 against the atrial face of the leaflets 110.

The position of the proximal sleeve 38 is also adjusted, then the inner sheath 94 is completely retracted. The distal sleeve 40 being positioned inside the proximal sleeve 38, it is kept in the contracted configuration by the proximal sleeve 38, which in turn is kept in the contracted configuration by the intermediate sleeve 95. This then leads to a configuration similar to that of FIG. 20.

By deploying inside the proximal sleeve 38, the distal sleeve 40 becomes connected to that proximal sleeve 38.

It will be noted that in this position, the leaflets 110 of the native valve are intercalated between the distal sleeve 40 and the proximal arms 20.

Once the proximal 38 and distal 40 sleeves are thus connected, the intermediate sheath 95 is retracted, so as to release the proximal sleeve 38, similarly to FIG. 21.

The proximal sleeve 38 then radially deploys as far as its deployed configuration, as well as the distal sleeve 40 inside that deployed proximal sleeve 38.

Once that is done, the axial fixing between the stent 93 and the proximal end is released. The stent 93, the head 92 and the rod are then removed outside the patient through the inner conduit, similarly to in FIG. 22.

The implant 12 in the deployed position is shown in FIG. 23. As before, in this deployed configuration, the distal sleeve 40 extends longitudinally or partially inside the proximal sleeve 38, coaxially to said proximal sleeve 38, partially inside the tissue receiving space 39, such that the tissue is received between the proximal arms 20 and the distal sleeve 40, and partially beyond the tissue receiving space 39.

It will be noted that the relative position of the proximal sleeve 38 with respect to the distal sleeve 40 is chosen during the installation of the implant 12, based on the configuration of the blood flow passage in which that implant 12 is installed. Thus, according to this embodiment, the proximal 38 and distal 40 sleeves are capable of sliding relative to one another.

It should be noticed that the proximal sleeve 38 is preferably arranged axially apart from the leaflets 110, inside the ventricular cavity, as shown in FIG. 23.

According to this alternative embodiment, each proximal arm 20 has a curved shape, with the convex side oriented radially away from the axis A-A'. In particular, the intermediate region 66 of each proximal end 20 comprises at least one proximal segment 72 diverging radially away from the connected end 62 and at least one distal segment 74 converging radially toward the free end 64. This curved shape makes it possible to define a longitudinal cavity 68 for receiving a valve leaflet 110, as previously described.

As previously indicated, the shape of the proximal arms 20 does not affect the method for inserting the implant, which may thus be similar to that described in reference to FIGS. 17 to 22, that described in reference to FIGS. 24 to 26, or any other possible insertion method.

Example shapes of proximal arms 20 will now be described, in reference to FIGS. 27 to 30. In these figures, the elements similar to those of the other figures are designated using identical references.

FIG. 27 shows an implant 12 according to another alternative embodiment of the proximal arms 20.

According to this alternative embodiment, each proximal arm 20 comprises:
a proximal part 106, leaving axially from the connected end 62 toward the proximal end 41 of the proximal sleeve 38,
a bifurcated part 108, connecting the proximal segment 106 to a distal part 116 of the proximal arm 20,
the distal part 116, leaving axially from the bifurcated part 108 toward the distal end of the proximal sleeve 38.

The distal part 116 may also have a curved shape 66 like that previously described in reference to FIG. 23.

The proximal part 106 and the bifurcated part 108 together define a deeper cavity for the leaflets 110. Of course, the length of the proximal part 106 may be chosen to be larger or smaller, based on the desired depth of the cavity 68.

FIG. 28 shows an implant 12 according to another alternative embodiment.

According to this alternative, at least one proximal end 20 has a distal region 70 protruding radially away from the central axis A-A relative to the intermediate region 66.

More particularly, at least one first proximal arm 20 has a first distal region 70 pressed across from a first distal arm 18, and a second proximal arm 20 has a second distal region 70 pressed across from a second distal arm 18, the radial expanse of the first distal region 70 being larger than the radial expanse of the second distal region 70.

Generally speaking, the radial expanse of the distal region 70 of each proximal arm 20 can be chosen to be larger or smaller, in particular based on the predetermined shape of the blood flow passage designed to receive the implant.

FIG. 29 shows a proximal sleeve 38 of an implant 12 according to another alternative embodiment.

According to this alternative, each proximal end 20 includes an intermediate part 118 elastically deformable in a longitudinal direction of the proximal arm 20. To that end, the intermediate part 118 is generally in the shape of a spring.

Owing to its longitudinally elastically deformable intermediate part 118, the length of each proximal end 20 can vary, and adapt based on the position of the proximal sleeve 38 relative to the distal sleeve 40, in particular to ensure optimal clamping of the leaflets 110 between the proximal arms 20 and the distal arms 18. In other words, in the absence of leaflets 110, it is possible to ensure contact between the free end 64 of at least one proximal arm 20 and one distal arm 18, in the deployed configuration and without any outside bias.

FIG. 3 shows a proximal sleeve 38 of an implant 12 according to another alternative embodiment.

According to this alternative, each proximal arm 20 includes an intermediate part 120 folded so as to form an axial return delimiting a hollow 122. This hollow 122 is designed to form a cavity for the leaflets 110.

FIGS. 31 and 32 show an implant 12 according to another alternative embodiment. In particular, the proximal sleeve 38 of the implant 12 is shown in FIG. 31, and the distal sleeve 40 in FIG. 32.

The proximal sleeve 38 is made up of filiform elements 34 arranged in a grid, for example forming diamond-shaped meshes.

As in particular shown in FIG. 31, the proximal sleeve 38 extends longitudinally between a proximal end 41 and a distal end 43 of the sleeve. Each proximal arm 20 extends between an end 62 connected to the distal end 43 of the proximal sleeve 38, and a free end 64. Thus, each proximal arm 20 extends in the direction of the central axis A-A' beyond that distal end 43 of the proximal sleeve 38.

According to this alternative embodiment, at least one proximal arm 20 has a length greater than that of at least one other proximal arm. Alternatively or in combination with said greater length, at least one proximal end 20 has a connected end 62 with a smaller width than that of the connected end 62 of at least one other proximal arm 20. Thus, the shapes of the proximal arms 20 may be adapted to the predetermined configuration of the blood flow passage designed to receive the implant 12.

Furthermore, the distal sleeve 40 is made up of undulating filiform elements 34. It will be noted that this distal sleeve 40 has an axial length greater than that of the distal sleeve that was described in reference to FIG. 4.

The proximal sleeve 38 is designed to be attached on the distal sleeve 40, and it is capable of sliding along the distal sleeve 40 until it is positioned in an optimal position relative to that distal sleeve 40, based on the configuration of the blood flow passage designed to receive the implant 12.

In the example shown in FIG. 32, the distal arms 18 extend continuously over the entire periphery of the distal sleeve 40 around the axis A-A' while being adjacent to one another.

Each distal arm 18 is formed by a loop 50A, 50B having two inner segments 52 shared with an adjacent distal arm 18, and one unique outer segment 54 folded in a loop.

As before, the distal arms 18 are movable between an axial position, shown in FIG. 32, when the implant 12 is in its contracted configuration, and a transverse position, when the implant 12 is in its deployed configuration.

In the transverse position, when idle, without any outside bias, each distal arm 18 extends perpendicular to the axis A-A'.

The shape and length of the distal arms 18 may vary from one arm to another, as shown in FIG. 32, in particular in order to adapt to the predetermined configuration of the blood flow passage designed to receive the implant 12.

It will be noted that the invention is not limited to the embodiments previously described, but may assume various alternatives without going beyond the scope of the claims.

In particular, it is possible to provide all sorts of adapted shapes for the proximal arms 20 and/or the distal arms 18.

For example, as an alternative to the upside down V-shaped proximal arms 20 previously described, the connected end 62 of which has a width larger than that of the free end 64, it is possible to provide at least one proximal arm with a flared shape, whereof the connected end 62 has a width smaller than that of the free end 64.

It is also alternatively possible to provide at least one proximal arm 20 with a rounded, half-circle or half-oval shape.

It also will be noted that other insertion method can be considered.

For instance, a treatment device similar to the treatment device of FIG. 24 also allows an insertion according to the following steps, shown on FIGS. 33 to 38.

First, the distal end of the tool 14, including the implant 12 in the contracted configuration, is inserted in the ventricular cavity.

Figure 33:
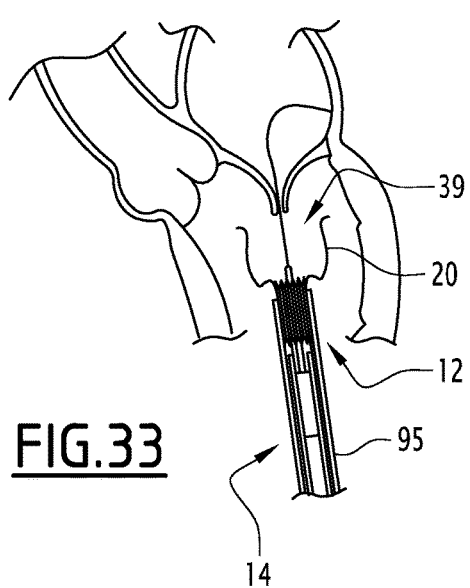

Then, as shown in FIG. 33, said other sheath 95 is axially retracted so as to release the proximal arms 20, which are then deployed, in particular by elasticity. The separation of the proximal arms 20 thus defines the receiving space 39, which is then completely free. It should be noticed that the proximal arms 20 are released before the body 30 be constituted. Indeed, the proximal arms 20 are released before the proximal sleeve 38 be assembled with the distal sleeve 40.

Figure 34:
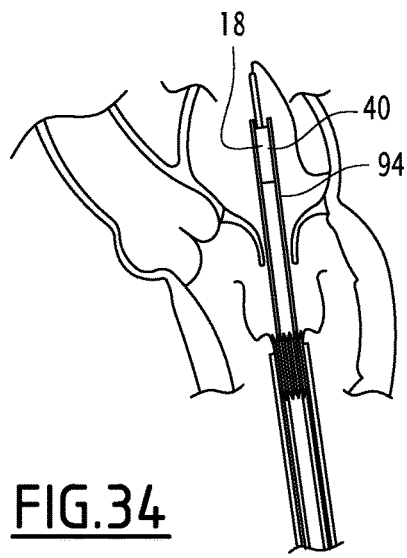

Then, as shown on FIG. 34, the inner sheath 94 containing the distal sleeve 40, is moved axially as far as the atrial cavity, beyond the mitral annulus, such that the distal arms 18 are positioned in the atrial cavity beyond the mitral annulus.

Figure 35:
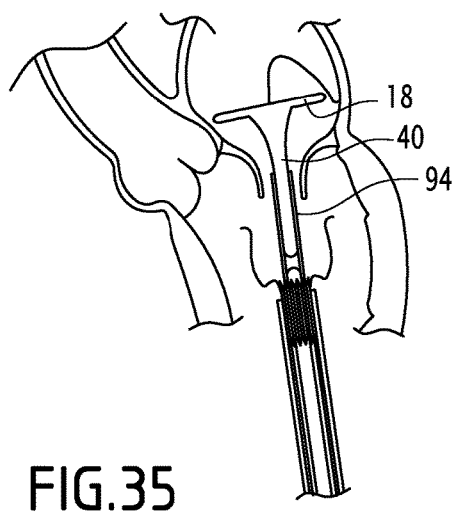

Next, as shown on FIG. 35, the inner sheath 94 is axially retracted so as to expose the distal arms 18, which are then deployed. During this step, the atrial sleeve 40 is still partially contracted in the inner sheath 94.

Figure 36:
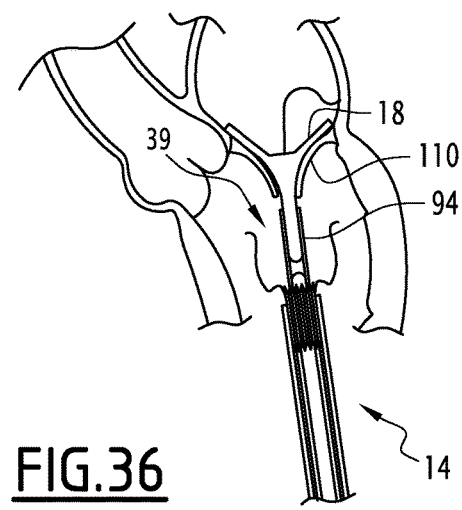

As shown on FIG. 36, the tool 14 is then moved toward the left ventricle to press the distal arms 18 against the atrial face of the leaflets 110. In other words, the distal arms 18 apply an axial force against the atrial face of the leaflets 110, this axial force being directed from the atrial cavity towards the ventricular cavity.

Figure 37:
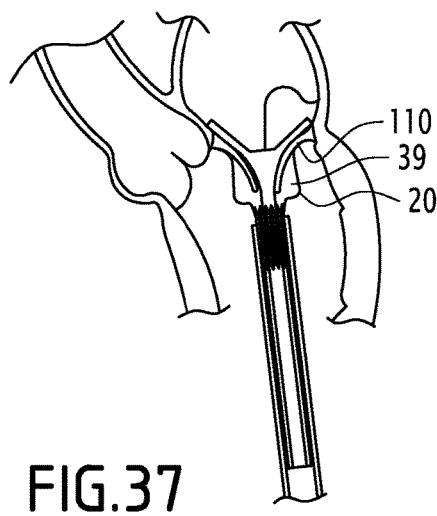

Then, the receiving space 39 is positioned across from the leaflets 110, such that they are inserted into the receiving space 39 by moving the deployment tool 14 toward those leaflets 110, as shown on FIG. 37. Thus, the proximal arms 20 are pressed against the ventricular face of the leaflets 110. In other words, the proximal arms 20 apply an axial force against the ventricular face of the leaflets 110, this axial force being directed from the ventricular cavity towards the atrial cavity. The direction of the force applied by the proximal arms 20 is opposed to the direction of the force applied by the distal arms 18.

We remind that the proximal sleeve 38 can slide relative to the distal sleeve 40, so that it is possible to choose the relative position of the proximal sleeve 38 with respect to the distal sleeve 40, based on the configuration of the blood flow passage in which that implant 12 is installed.

Figure 38:
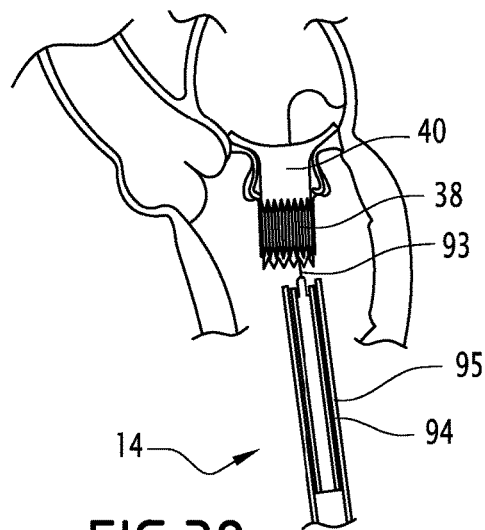

Thus, the position of the proximal sleeve 38 is adjusted, then the inner sheath 94 and the other sheath 95 are retracted, so that the distal sleeve 40 and the proximal sleeve 38 are deployed, as shown on FIG. 38. It should be noticed that the distal sleeve 40 and the proximal sleeve 38 can be deployed simultaneously, or, in a variant, the distal sleeve 40 is deployed into the proximal sleeve 38 previously to the deployment of this proximal sleeve 38.

After the deployment of the proximal sleeve 38 and the distal sleeve 40, said proximal sleeve 38 and distal sleeve 40 are assembled together, thus they form the body 30. In other words, the body 30 (thus the tubular frame 16) is formed only in the deployed configuration.

Once that is done, the axial fixing between the stent 93 and the proximal end is released. The tool 14 is then removed outside the patient through the inner conduit.

Other insertion method can be considered.

More particularly, since the implant 12 is made of two independent parts 38, 40, these two parts may be brought by different ways into the blood flow passage. For instance, a combined retrograde and anterograde procedure could be performed, as shown on FIGS. 39 to 44.

First, a first part 14A of the tool, comprising said other sheath 95, and the proximal sleeve 38 in the contracted configuration within the other sheath 95, are introduced in the ventricular cavity from a first way.

Figure 39:
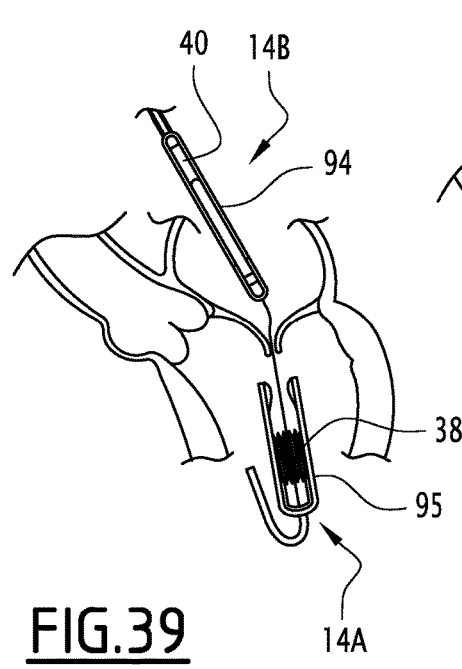

Then, as shown on FIG. 39, a second part 14B of the tool, comprising the inner sheath 94, and the distal sleeve 40 in the contracted configuration within the inner sheath 94, is introduced in the atrial cavity, from a second way different from said first way from which the first part of the tool is introduced in the ventricular cavity. Thus, in this procedure, the second part of the tool is not inserted in the atrial cavity through the mitral annulus.

Then, the other sheath 95 is axially retracted so as to release the proximal arms 20, which are then deployed, in particular by elasticity. The separation of the proximal arms 20 thus defines the receiving space 39.

Figure 40:
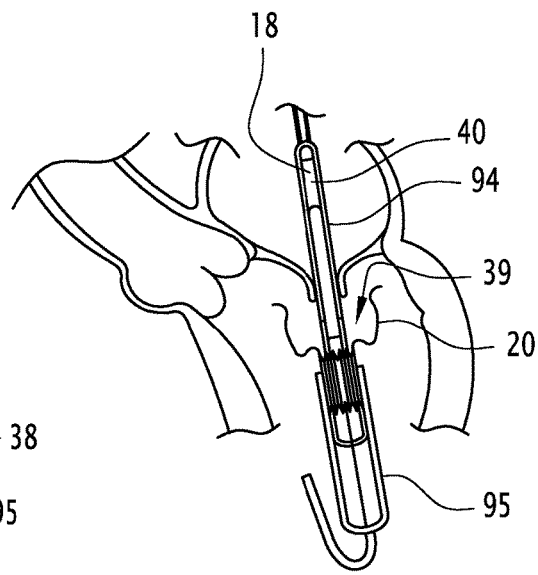

Then, as shown on FIG. 40, the inner sheath 94 containing the distal sleeve 40 is moved axially as far as the ventricular cavity, beyond the mitral annulus, such that the distal arms 18 are positioned in the atrial cavity, and the distal sleeve 40 is partially positioned in the ventricular cavity.

Figures 41, 42:
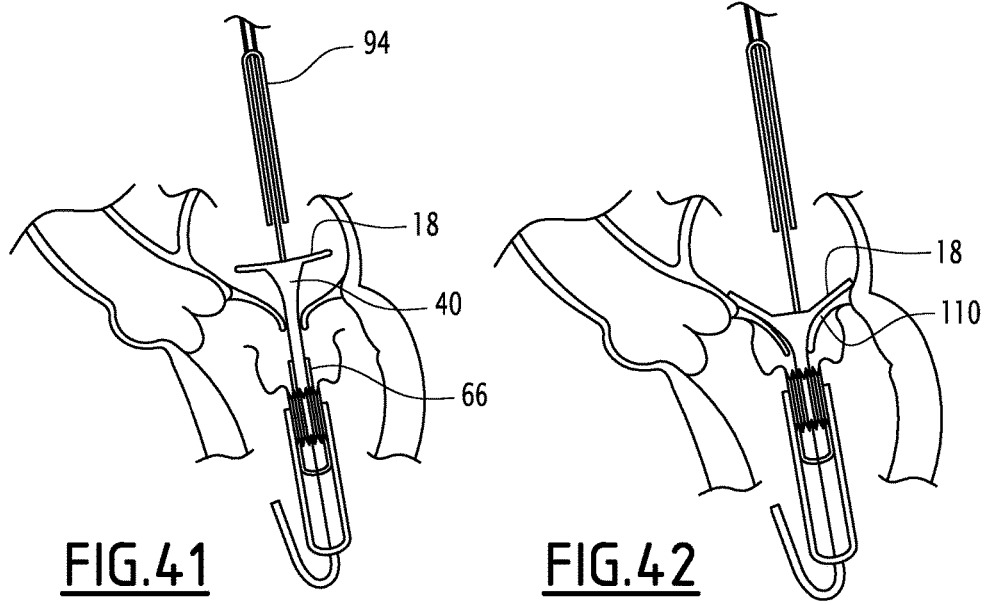

Next, as shown on FIG. 41, the inner sheath 94 is axially retracted so as to expose the distal arms 18, which thus are deployed. During this step, the distal sleeve 40 is still partially contracted by means of an annular maintainer 66 surrounding the atrial sleeve 40.

The distal arms 18 are then pressed against the atrial face of the leaflets 110, as shown on FIG. 42. In other words, the distal arms 18 apply an axial force against the atrial face of the leaflets 110, this axial force being directed from the atrial cavity towards the ventricular cavity. Then, the receiving space 39 is positioned across from the leaflets 110, such that they are inserted into the receiving space 39 by moving the first part 14A of the deployment tool 14 toward those leaflets 110, as shown on FIG. 43. Thus, the proximal arms 20 are pressed against the ventricular face of the leaflets 110. In other words, the proximal arms 20 apply an axial force against the ventricular face of the leaflets 110, this axial force being directed from the ventricular cavity towards the atrial cavity. The direction of the force applied by the proximal arms 20 is opposed to the direction of the force applied by the distal arms 18.

We remind that the proximal sleeve 38 can slide relative to the distal sleeve 40, so that it is possible to choose the relative position of the proximal sleeve 38 with respect to the distal sleeve 40, based on the configuration of the blood flow passage in which that implant 12 is installed.

Figures 43, 44:
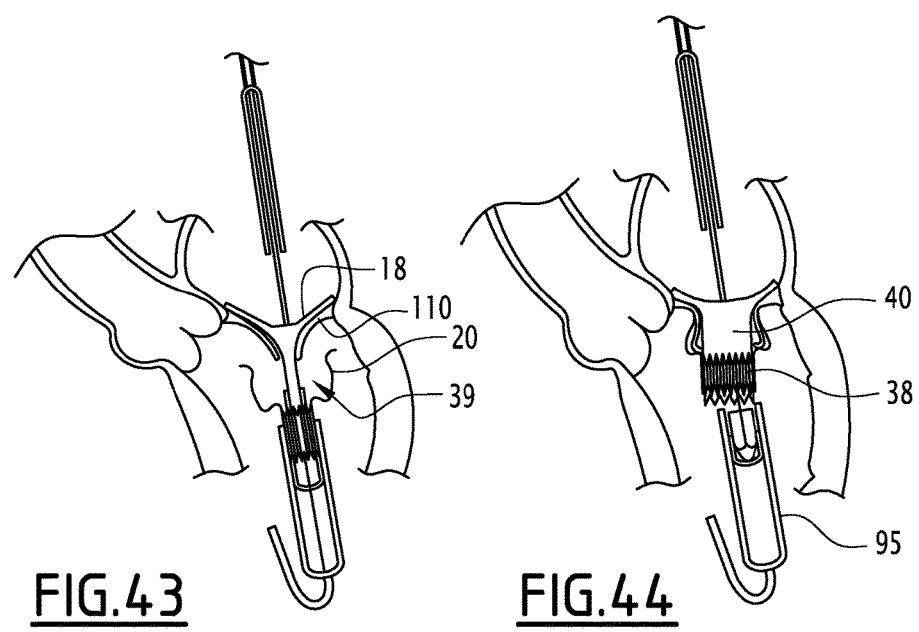

Thus, the position of the proximal sleeve 38 is adjusted, then the annular maintainer 66 and the other sheath 95 are retracted, so that the distal sleeve 40 and the proximal sleeve 38 are deployed, as shown on FIG. 44. It should be noticed that the distal sleeve 40 and the proximal sleeve 38 can be deployed simultaneously, or, in a variant, the distal sleeve 40 is deployed into the proximal sleeve 38 previously to the deployment of this proximal sleeve 38.

Once that is done, the tool 14 is then removed outside the patient.

The invention claimed is:

1. An implant designed to be placed in a blood flow passage and to be fixed on a tissue, the implant being deployable between a contracted configuration and a deployed configuration, the implant comprising:
   a tubular frame along a central axis, defining an inner blood flow conduit, the tubular frame extending between a proximal end and a distal end, the tubular frame comprising a first part and a second part, said first and second parts being separated and said first and second parts being assemblable so as to form the tubular frame when assembled;
   a plurality of distal arms extending perpendicular to the central axis in the deployed configuration to press on a first face of the tissue;
   a plurality of proximal arms having one end connected to the frame and one free end (64) designed to press on a second face of the tissue to clamp the tissue;
   wherein:
   the implant comprises a first integral assembly including the first part of the frame and the proximal arms, and a second integral assembly including the second part of the frame and the distal arms, the first assembly and the second assembly being attached one on top of the other;
   the first part of the frame is in the form of a proximal sleeve, with the central axis, extending longitudinally between a proximal end and a distal end of the sleeve;
   each proximal arm is elastically deformable towards a rest position; and
   the connected end of each proximal arm is connected to the distal end of the proximal sleeve, and the free end of each proximal arm extends in the direction of the central axis beyond that distal end of the proximal sleeve when this proximal arm is in the rest position.

2. The implant according to claim 1, wherein, the proximal arms delimiting a space between them for receiving the tissue, the proximal sleeve extends completely outside that receiving space.

3. The implant according to claim 1, wherein the first and second parts of the frame are each formed by a mesh of interlaced threads.

4. The implant according to claim 1, wherein:
the proximal arms delimit a space between them for receiving the tissue,
the second part of the frame is in the form of a distal sleeve, with the central axis, said distal sleeve extending longitudinally:
partially inside the proximal sleeve, coaxially to the proximal sleeve;
partially inside the space for receiving the tissue, such that the tissue is capable of being received between the proximal arms and the distal sleeve; and
partially beyond the tissue receiving space.

5. The implant according to claim 4, wherein the proximal sleeve has, when it is separated from the distal sleeve, and when no outside bias is present, a diameter smaller than that of the distal sleeve when no outside bias is present.

6. The implant according to claim 1, wherein, in the deployed configuration, when no outside bias is present, the free end of at least one proximal arm is positioned in contact with the distal arm and/or the frame, the proximal arm including at least one intermediate region extending along and radially separated from the frame to define a longitudinal cavity for receiving the tissue.

7. The implant according to claim 6, wherein the intermediate region of each proximal arm has a curved shape, with the convex side oriented radially away from the central axis, the intermediate region comprising at least one proximal segment diverging radially away from the connected end and at least one distal segment converging radially toward the free end.

8. The implant according to claim 6, wherein at least one proximal arm defines, at its free end, a distal region protruding radially away from the central axis relative to the intermediate region, the distal region being pressed below a distal arm, the stiffness in flexure of the intermediate region being greater than the stiffness in flexure of the distal region.

9. The implant according to claim 1, wherein each proximal arm has two branches distally converging toward one another to substantially assume the shape of an upside down V in the deployed configuration.

10. The implant according to claim 1, wherein each distal arm forms a loop protruding transversely relative to the central axis.

11. The implant according to claim 10, wherein the distal arms are adjacent to one another to form a transverse collar perpendicular to the axis in the deployed configuration, the collar advantageously being covered with a skirt made from tissue capable of guiding the blood through the frame.

12. The implant according to claim 1, wherein the radial expanse of a first distal arm in a first annular sector around the central axis is greater than the radial expanse of a second distal arm situated in a second annular sector, advantageously greater than 50% of the radial expanse of a second distal arm.

13. The implant according to claim 1, wherein at least one first proximal arm has a first distal region pressed across from a first distal arm, a second proximal arm having a second distal region pressed across from a second distal arm, the radial expanse of the first distal region being greater than the radial expanse of the second distal region.

* * * * *